US009200287B2

(12) United States Patent
Uhlmann et al.

(10) Patent No.: US 9,200,287 B2
(45) Date of Patent: *Dec. 1, 2015

(54) PHOSPHATE-MODIFIED OLIGONUCLEOTIDE ANALOGS WITH ENHANCED IMMUNOSTIMULATORY ACTIVITY

(75) Inventors: Eugen Uhlmann, Glashuetten (DE); Marion Jürk, Dormagen (DE)

(73) Assignee: AdiuTide Pharmaceuticals GmbH, Frankfurt (DE)

( * ) Notice: Subject to any disclaimer, the term of this patent is extended or adjusted under 35 U.S.C. 154(b) by 339 days.

This patent is subject to a terminal disclaimer.

(21) Appl. No.: 12/600,368

(22) PCT Filed: May 15, 2008

(86) PCT No.: PCT/IB2008/001206
§ 371 (c)(1),
(2), (4) Date: Nov. 16, 2009

(87) PCT Pub. No.: WO2008/142513
PCT Pub. Date: Nov. 27, 2008

(65) Prior Publication Data
US 2010/0261779 A1 Oct. 14, 2010

Related U.S. Application Data

(60) Provisional application No. 60/930,764, filed on May 18, 2007.

(51) Int. Cl.
A61K 48/00 (2006.01)
C07H 21/02 (2006.01)
C12N 15/117 (2010.01)
A61K 31/7125 (2006.01)
A61K 45/06 (2006.01)

(52) U.S. Cl.
CPC .......... *C12N 15/117* (2013.01); *A61K 31/7125* (2013.01); *A61K 45/06* (2013.01); *C12N 2310/17* (2013.01); *C12N 2310/311* (2013.01); *C12N 2310/315* (2013.01); *C12N 2310/3125* (2013.01)

(58) Field of Classification Search
CPC ...................... C12N 2310/315; C12N 2310/17; C12N 2310/346; C12N 2310/31; C12N 15/113; C12N 15/1138; C12N 15/117; C12N 15/111; C12N 2320/51; A61K 2039/55561; A61K 2039/53; A61K 39/39; A61K 31/7125; A61K 2300/00
See application file for complete search history.

(56) References Cited

U.S. PATENT DOCUMENTS

| 4,469,863 | A | | 9/1984 | Ts'o et al. ........................ 536/27 |
| 5,023,243 | A | | 6/1991 | Tullis ............................... 514/44 |
| 5,284,656 | A | | 2/1994 | Platz et al. ...................... 424/435 |
| 5,451,569 | A | | 9/1995 | Wong et al. ........................ 514/3 |
| 5,658,738 | A | | 8/1997 | Nadeau et al. .................... 435/6 |
| 5,668,265 | A | | 9/1997 | Nadeau et al. ................. 536/23.1 |
| 5,912,332 | A | * | 6/1999 | Agrawal et al. ............... 536/23.1 |
| 6,194,388 | B1 | | 2/2001 | Krieg et al. ....................... 514/44 |
| 6,207,646 | B1 | | 3/2001 | Krieg et al. ....................... 514/44 |
| 6,214,806 | B1 | | 4/2001 | Krieg et al. ....................... 514/44 |
| 6,218,371 | B1 | | 4/2001 | Krieg et al. ....................... 514/44 |
| 6,239,116 | B1 | | 5/2001 | Krieg et al. ....................... 514/44 |
| 6,339,068 | B1 | | 1/2002 | Krieg et al. ....................... 514/44 |
| 6,406,705 | B1 | | 6/2002 | Davis et al. ................. 424/278.1 |
| 6,429,199 | B1 | | 8/2002 | Krieg et al. ....................... 514/44 |
| 6,693,187 | B1 | | 2/2004 | Dellinger ...................... 536/25.3 |
| 2003/0148976 | A1 | | 8/2003 | Krieg et al. ....................... 514/44 |
| 2004/0198688 | A1 | | 10/2004 | Krieg et al. ....................... 514/44 |
| 2005/0130911 | A1 | * | 6/2005 | Uhlmann et al. ................. 514/26 |
| 2005/0266422 | A1 | * | 12/2005 | Vagle et al. ........................ 435/6 |
| 2006/0019916 | A1 | | 1/2006 | Krieg et al. ....................... 514/44 |
| 2006/0172966 | A1 | * | 8/2006 | Lipford et al. .................... 514/44 |
| 2008/0045473 | A1 | | 2/2008 | Uhlmann et al. ................. 514/44 |

FOREIGN PATENT DOCUMENTS

| EP | 0092574 B1 | 4/1992 | |
| WO | WO8301451 | 4/1983 | ............. C07H 21/04 |
| WO | WO9524929 | 9/1995 | ............. A61K 48/00 |
| WO | WO9703702 | 2/1997 | ............. A61K 48/00 |
| WO | WO0122990 | 4/2001 | ............. A61K 38/21 |
| WO | WO0232912 | 4/2002 | |
| WO | WO03086280 | 10/2003 | |
| WO | WO2004005476 | 1/2004 | |
| WO | WO2006116458 | 11/2006 | |

OTHER PUBLICATIONS

Benjamin Douglas Lunstad, Synthesis and characterization of novel DNA based dendrimers, 2002, PhD dissertation, Graduate School of the University of Colorado, total 147 pages, the dissertation ends with page No. 131.*
Charlie Schmidt, Clinical setbacks for toll-like receptor 9 agonists in cancer, 2007, Nature Biotechnology, vol. 25, pp. 825-826.*
Ilvesaro et al., Toll like receptor-9 agonists stimulate prostate cancer invasion in vivo, 2007, The Prostate, vol. 67, pp. 774-781.*
Ren et al., TLR9 signaling promotes tumor progression of human lung cancer cell in vivo, 2009, Pathology & Oncology Research, vol. 15, pp. 623-630.*
Tokunaga, T., et al., "A Synthetic Single-Stranded DNA, Poly (dG,dC), Induces Interferon-$\alpha$/$\beta$ and —$_{3}$, Augments Natural Killer Activity, and Suppresses Tumor Growth", Japan Journal of Cancer Research, Jun. 1988, pp. 682-686, vol. 79.
Tokunaga, T., et al., "Antitumor Activity of Deoxyribonucleic Acid Fraction From Mycobacterium bovis BCG. I. Isolation, Physicochemical Characterization, and Antitumor Activity[1,2]", JNCI, Apr. 1984, pp. 955-962, vol. 72, No. 4.
Messina, J., et al., "Stimulation of In Vitro Murine Lymphocyte Proliferation by Bacterial Dna[1]", Journal of Immunology, Sep. 15, 1991, pp. 1759-1764, vol. 147, No. 6.

(Continued)

Primary Examiner — Dana Shin
(74) Attorney, Agent, or Firm — Chalin A. Smith; Smith Patent

(57) ABSTRACT

The invention relates to oligonucleotides including at least one backbone modification and a pyrimidine-purine dinucleotide. The invention also relates to pharmaceutical compositions and methods of use thereof.

11 Claims, 9 Drawing Sheets

(56) References Cited

OTHER PUBLICATIONS

Krieg, Arthur M., "Leukocyte Stimulation by Oligodeoxynucleotides", In: Applied Antisense Oligonucleotide Technology, 1998, pp. 431-448, Chapter 24.

Krieg, A. M., et al., "CpG motifs in bacterial DNA trigger direct B-cell activation", Nature, Apr. 6, 1995, pp. 546-549, vol. 374.

Krieg, A.M., et al., "Mechanisms and applications of immune stimulatory CpG oligodeoxynucleotides", Biochimics et Biophysica Acta, 1999, pp. 107-116, vol. 1489.

Hartmann, G., et al., "CpG DNA: A potent signal for growth, activation, and maturation of human dendritic cells", Proceeding of National Academy of Sciences of the United States of America, Aug. 3, 1999, pp. 9305-9310, vol. 96.

Pisetsky, David S., "The Immunologic Properties of DNA[1]", The Journal of Immunology, Jan. 15, 1996, pp. 421-423, vol. 156.

Häcker, H., et al., "CpG-DNA-specific activation of antigen-presenting cells requires stress kinase activity and is preceded by non-specific endocytosis and endosomal maturation", The EMBO Journal, Nov. 2, 1998, pp. 6230-6240, vol. 17, No. 21.

Lipford, G.B., et al., "Bacterial DNA as immune cell activator", Trends in Microbiology, Dec. 1, 1998, pp. 496-500, vol. 6, No. 12.

Yi, Ae-Kyung, et al., "CpG Oligodeoxyribonucleotides Rescue Mature Spleen B Cells from Spontaneous Apoptosis and Promote Cell Cycle Entry[1]", The Journal of Immunology, Jun. 15, 1998, pp. 5898-5906, vol. 160.

Liang, H., et al., "Activation of Human B Cells by Phosphorothioate Oligodeoxynucleotides", Journal of Clinical Investigation, Sep. 1, 1996, pp. 1119-1129, vol. 98, No. 5.

Wagner, R.W., et al., "Potent and selective inhibition of gene expression by an antisense heptanucleotide", Nature Biotechnology, Jul. 1996, pp. 840-844, vol. 14, No. 7.

Ballas, Z.K., et al., "Induction on NK Activity in Murine and Human Cells by CpG Motifs in Oligodeoxynucleotides and Bacterial DNA[1]" Journal of Immunology, Sep. 1, 1996, pp. 1840-1845, vol. 157, No. 5.

Yamamoto, S., et al., "Unique Palindromic Sequences in Synthetic Oligonucleotides are Required to Induce INF and Augment INF-Mediated Natural Killer Activity[1]", The Journal of Immunology, Jun. 15, 1992, pp. 4072-4076, vol. 148, No. 12.

Uhlmann, E., et al., "Antisense Oligonucleotides: A New Therapeutic Principle", Chemical Reviews, Jun. 1990, pp. 543-584, vol. 90, No. 4.

Goodchild, John, "Conjugates of Oligonucleotides and Modified Oligonucleotides: A Review of Their Synthesis and Properties", Bioconjugate Chemistry, May/Jun. 1990, pp. 165-187, vol. 1, No. 3.

Uhlmann, E. et al., "Oligonucleotide Analogs Containing Dephospho-Internucleoside Linkages", Methods in Molecular Biology, 1993, pp. 355-389, Chapter 16, vol. 20.

Crooke, S.T., et al., "Progress in Antisense Oligonucleotide Therapeutics" Annual Review of Pharmacology and Toxicology, Apr. 1996, pp. 107-129, vol. 36.

Hunziker, J., et al., "Nucleic Acid Analogues: Synthesis and Properties", Modern Synthesis Methods, 1995, pp. 331-417, vol. 7.

Stirchak, E.P., et al., "Uncharged stereoregular nucleic acid analogs: 2. Morpholino nucleoside oligomers with carbamate internucleoside linkages", Nucleic Acids Research, Jun. 1989, pp. 6129-6141, vol. 17, No. 15.

Nielsen, P.E., et al., "Peptide Nucleic Acid (PNA). A DNA Mimic with a Peptide Backbone", Bioconjugate Chemistry, Jan. 1994, pp. 3-7-, vol. 5, No. 1.

Froehler, B., et al., "Triple-Helix Formation by Oligodeoxynucleotides Containing the Carbocyclic Analogs of Thymidine and 5-Methyl-2'-deoxycytidine", Journal American Chemical Society, 1992, pp. 8320-8322, vol. 114.

Vandendriessche, F., et al., "Acyclic Oligonucleotides: Possibilities and Limitations", Tetrahedron, Aug. 20, 1993, pp. 7223-7238, vol. 49, No. 33.

Tarköy, M., et al., Nucleic-Acid Analogues with Constraint Conformational Flexibility in the Sugar-Phosphate Backbone ('Bicyclo-DNA'), Helvetica Chimica Acta, 1993, pp. 481-510, vol. 76, No. 1.

Seliger, H., et al., "Oligonucleotide Analogues with Terminal 3'-3' and 5'-5'-Internucleotidic Linkages As Antisense Inhibtors of Viral Gene Expression", Nucleosides & Nucleotides, 1991, pp. 469-477, vol. 10, No. 1-3.

Jiang, Z., et al., "Pseudo-Cyclic Oligonucleotides: In Vitro and In Vivo Properties", Bioorganic & Medicinal Chemistry, Dec. 1999, pp. 2727-2735, vol. 7, No. 12.

Durand, M., et al., "Triple-Helix Formation by an Oligonucleotide Containing One $(dA)_{12}$ and Two $(dT)_{12}$ Sequences Bridged by Two Hexaethylene Glycol Chains", Biochemistry, Sep. 1992, pp. 9197-9204, vol. 31, No. 38.

Fontanel, Marie-Laurence, et al., "Sterical recognition by $T_4$ polynucleotide kinase of non-nucleosidic moieties 5'-attached to oligonucleotides", Nucleic Acids Research, 1994, pp. 2022-2027, vol. 22, No. 11.

Vallin, H., et al., "Anti-Double-Stranded DNA Antibodies and Immunostimulatory Plasmid DNA in Combination Mimic the Endogenous IFN-α Inducer in Systemic Lupus Erythematosus[1]", The Journal of Immunology, Dec. 1, 1999, pp. 6306-6313, vol. 163, No. 11.

Hoet, R.M.A., et al., "The Importance of the Light Chain for the Epitope Specificity of Human Anit-U1 Small Nuclear RNA Autoantibodies Present in Systemic Lupus Erythematosus Patients[1]", The Journal of Immunology, Sep. 15, 1999, pp. 3304-3312, vol. 163, No. 6.

Van Venrooij, W.J., et al., "Anti-(U1) Small Nuclear RNA Antibodies in Anti-Small Nuclear Ribonucleoprotein Sera from Patients with Connective Tissue Diseases", Journal of Clinical Investigation, Dec. 1990, pp. 2154-2160, vol. 86, No. 6.

Plotz, P.H., et al., "The role of autoantigens in the induction and maintenance of autoimmunity", Molecular Biology Reports, 1992, pp. 127-132, vol. 16.

Mohan, C., et al., "Nucleosome: A Major Immunogen for Pathogenic Autoantibody-inducing T Cells of Lupus", Journal of Experimental Medicine, May 1993, pp. 1367-1381, vol. 177, No. 5.

Fatenejad, S., et al., "Pattern of Anti-Small Nuclear Ribonucleoprotein Antibodies in MRL/MP-*Ipr/Ipr* Mice Suggest That the Intact U1 snRNP Particle Is Their Autoimmunogenic Target[1]", The Journal of Immunology, Jun. 1, 1994, pp. 5523-5531, vol. 152, No. 11.

Malmegrim, K.C.R, et al., "The Fate of the U1 snRNP Autoantigen during Apoptosis: Implications for Systemic Autoimmunity", Israel Medical Association Journal, Sep. 2002, pp. 706-712, vol. 4, No. 9.

Newkirk, M.M, et al., "Autoimmune Response to U1 Small Nuclear Ribonucleoprotein (U1 snRNP) Associated with Cytomegalovirus Infection", Arthritis Research, 2001, pp. 253-258, vol. 3, No. 4.

Magnusson, M., et al., "Importance of CpG Dinucleotides in Activation of Natural IFN-α-Producing Cells by a Lupus-Related Oligodeoxynucleotide", Scand. Journal of Immunology, 2001, pp. 543-550, vol. 54, No. 6.

Rönnblom, L., et al., "A Pivotal Role for the Natural Interferon α-producing Cells (Plasmacytoid Dendritic Cells) in the Pathogenesis of Lupus", Journal of Experimental Medicine, Dec. 17, 2001, pp. F59-F63, vol. 194, No. 12.

Tsai, D.E., et al., "In vitro selection of an RNA epitope immunologically cross-reactive with a peptide", Proceeding National Academy of Science, Oct. 1992, pp. 8864-8868, vol. 89, No. 19.

Tsai, D. E., et al., "In Vitro Selection of RNA Epitopes Using Autoimmune Patient Serum[1]", The Journal of Immunology, Feb. 1, 1993, pp. 1137-1145, vol. 150, No. 3.

Cohen, P.A., et al., "DC4+ T-Cells from Mice Immunized to Syngeneic Sarcomas Recognize Distinct, Non-Shared Tumor Antigens", Cancer Research, Feb. 15, 1994, pp. 1055-1058, vol. 54, No. 4.

Barnes, P.J., et al., "Efficacy and Safety of Inhaled Corticosteroids in Asthma", American Review of Respiratory Disease, 1993, pp. S1-S26, vol. 148.

Kamada, A.K., et al., "Issues in the use of inhaled glucocorticoids. The Asthma Clinical Research Network", American Journal of Respiratory and Critical Care Medicine, Jun. 1996, pp. 1739-1748, vol. 153, No. 6.

Gregoriadis, G., "Liposomes for drugs and vaccines", Trends in Biotechnology, Sep. 1985, pp. 235-241, vol. 3 No. 9.

(56) References Cited

OTHER PUBLICATIONS

Chickering, D., et al., "Poly(fumaric-co-sebacic) Microspheres as Oral Drug Delivery Systems", Biotechnology and Bioengineering, 1996, pp. 96-101, vol. 52, No. 1.
Mathiowitz, E., et al., "Biologically erodable microspheres as potential oral drug delivery systems", Nature, Mar. 27, 1997, pp. 410-414, vol. 386, No. 6623.
Sawhney, H.S., et al., "Bioerodible Hydrogels Based on Photopolymerized Poly(ethylene glycol)-co-poly(α-hydroxy acid) Diacrylate Macromers", Macromolecules, Feb. 1993, pp. 581-587, vol. 26.
Abuchowski, A., et al., "Soluble Polymer-Enzyme Adducts", Enzymes as Drugs, 1981, Chapter 13, pp. 367-383, Holcenberg and Roberts, eds., Wiley-Interscience publication, John Wiley & Sons Inc., New York, New York.
Newmark, et al., "Preparation and Properties of Adducts of Streptokinase and Streptokinase-Plasmin Complex with Polyethylene Glycol and Pluronic Polyol F38", Journal of Applied Biochemistry, 1982, pp. 185-189, vol. 4.
Adjei, A., et al., "Pulmonary Delivery of Peptide Drugs: Effect of Particle Size on Bioavailability of Leuprolide Acetate in Healthy Male Volunteers", Pharmaceutical Research, 1990, pp. 565-569, vol. 7, No. 6.
Adjei, A., et al., "Bioavailability of Leuprolide Following Intratracheal Administration of Beagle Dogs", International Journal of Pharmaceutics, Jun. 11, 1990, pp. 135-144, vol. 61, Issues 1-2.
Braquet, P., et al., "Effect of Endothelin-1 on Blood Pressure and Bronchopulmonary System of the Guinea Pig", Journal of Cardiovascular Pharmacology, 1989, pp. S143-S146, vol. 13, Suppl. 5.
Hubbard, R., et al., "Anti-Neutrophil-Elastase Defenses of the Lower Respiratory Tract in α 1-Antitrypsin Deficiency Directly Augmented with an Aerosol of α 1-Antitrypsin", Annals of Internal Medicine, Aug. 1, 1989, pp. 206-212, vol. 111, No. 3.
Smith, R., et al., "Pulmonary Deposition and Clearance of Aerosolized Alpha-1-Proteinase Inhibitor Administered to Dogs and to Sheep", Journal of Clinical Investigation, Oct. 1989, pp. 1145-1154, vol. 84, No. 4.
Oeswein, J., et al., "Aeroxolization of Protein Pharmaceuticals", Proceedings of Symposium on Respiratory Drug Delivery II, Mar. 1990, pp. 1-34, Keystone, Colorado.
Debs, R.J., et al., "Lung-Specific Delivery of Cytokines Induces Sustained Pulmonary and Systemic Immunomodulation in Rats[1]", The Journal of Immunology, May 15, 1988, pp. 3482-3488, vol. 140, No. 10.
Langer R., "New Methods of Drug Delivery", Science, Sep. 28, 1990, pp. 1527-1533, vol. 249.
Dellinger, D., et al., "Oligodeoxyribonucleotide Analogs Functionalized with Phosphonacetate and Thiophosphonoacetate Diesters", Current Protocols in Nucleic Acid Chemistry, Oct. 2004, pp. Unit 4.24.1-4.24.26, vol. Chapter 4, Supplement 18.
Sheehan, D., et al., "Biochemical Properties of Phosphonoacetate and Thiophosphonoacetate Oligodeoxyribonucleotides", Nucleic Acids Research, Jul. 15, 2003, pp. 4109-4118, vol. 31, No. 14.
Rudolph, J.M, et al., "Phosponoacetate Derivatives of Oligodeoxyribonucleotides", Nucleosides & Nucleotides, Jan. 1, 1996, pp. 1725-1739, vol. 15, No. 11-12.
Mutwiri, G.K., et al., "Strategies for Enhancing the Immunostimulatory Effects of CpG Oligodeoxynucleotides", Journal of Controlled Release, May 31, 2004, pp. 1-17, vol. 97, No. 1.
PCT International Search Report, PCT/IB2008/001206, WO 2008/142513, 4 pages, Jul. 2, 2009 date of search.
U.S. Appl. No. 60/313,273, "Combination Motif Immune Stimulatory Oligonucleotides with Improved Activity", filed Aug. 17, 2001.
Agrawal, S. et al., "Synthetic Agonists of Toll-like receptors 7, 8, and 9", *Biochemical Society Transactions* (2007), vol. 13, part 6, pp. 1461-1466.
Elkins, K. et al., "Bacterial DNA Containing CpG Motifs Stimulates Lymphocyte-Dependent Protection of Mice Against Lethal Infection with Intracellular Bacteria", *Journal of Immunology* (1999), vol. 162, pp. 2291-2298.
Jurk, M. et al., "Structure-Activity Relationship Studies on the Immune Stimulatory Effects of Base-Modified CpG Toll-like Receptor 9 Agonists", ChemMedChem (2006), vol. 1, pp. 1007-1014.
Sonehara, K. et al., "Hexamer Palindromic Oligonucleotides with 5'-CG-3' Motifs Induce Production of Interferon", *Journal of Interferon and Cytokine Research* (1996), vol. 16, pp. 799-803.
Vandendriessche, F. et al., "Acyclic Oligonucleotides: Possibilities and Limitations", Tetrahedron (1993), vol. 49, No. 33, pp. 7273-7238.
Verthelyi, D. et al, "Immunoregulatory Activity of CpG Oligonucleotides in Humans and Nonhuman Primates", *Clinical Immunology* (2003), vol. 109, pp. 64-71.
Vollmer, Jörg, "Progress in Drug Development of Immunostimulatory CpG Oligonucleotide Ligands for TLR9", *Expert Opinion on Biological Therapy* (2005), vol. 5, No. 5, pp. 673-682.
Vollmer, Jörg, "CpG Motifs to Modulate Innate and Adaptive Immune Responses", *International Reviews of Immunology* (2006), vol. 25, pp. 125-134.

* cited by examiner

PHOSPHATE-MODIFIED OLIGONUCLEOTIDE ANALOGS WITH ENHANCED IMMUNOSTIMULATORY ACTIVITY

This application corresponds to the national phase of International Application No. PCT/IB2008/001206 filed May 15, 2008, which, in turn, claims priority to U.S. Provisional Application No. 60/930,764 filed May 18, 2007, the contents of which are incorporated by reference herein in their entirety.

FIELD OF THE INVENTION

The invention related to oligonucleotides having at least one phosphonoacetate or phosphonoacetate-like linkage.

BACKGROUND AND METHODS OF USE

Bacterial DNA has immune stimulatory effects to activate B cells and natural killer cells, but vertebrate DNA does not (Tokunaga, T., et al., 1988. *Jpn. J. Cancer Res.* 79:682-686; Tokunaga, T., et al., 1984, *JNCI* 72:955-962; Messina, J. P. et al., 1991, *J. Immunol.* 147:1759-1764; and reviewed in Krieg, 1998, In: Applied Oligonucleotide Technology, C. A. Stein and A. M. Krieg, (Eds.), John Wiley and Sons, Inc., New York, N.Y., pp. 431-448). It is now understood that these immune stimulatory effects of bacterial DNA are a result of the presence of unmethylated CpG dinucleotides in particular base contexts (CpG motifs), which are common in bacterial DNA, but methylated and underrepresented in vertebrate DNA (Krieg et al., 1995 Nature 374:546-549; Krieg, 1999 Biochim. Biophys. Acta 93321:1-10). The immune stimulatory effects of bacterial DNA can be mimicked with synthetic oligodeoxynucleotides (ODN) containing these CpG motifs. Such CpG ODN have highly stimulatory effects on human and murine leukocytes, inducing B cell proliferation; cytokine and immunoglobulin secretion; natural killer (NK) cell lytic activity and IFN-γ secretion; and activation of dendritic cells (DCs) and other antigen presenting cells to express costimulatory molecules and secrete cytokines, especially the Th1-like cytokines that are important in promoting the development of Th1-like T cell responses. These immune stimulatory effects of native phosphodiester backbone CpG ODN are highly CpG specific in that the effects are dramatically reduced if the CpG motif is methylated, changed to a GpC, or otherwise eliminated or altered (Krieg et al., 1995 Nature 374:546-549; Hartmann et al., 1999 Proc. Natl. Acad. Sci. USA 96:9305-10).

In early studies, it was thought that the immune stimulatory CpG motif followed the formula purine-purine-CpG-pyrimidine-pyrimidine (Krieg et al., 1995 Nature 374:546-549; Pisetsky, 1996 J. Immunol. 156:421-423; Hacker et al., 1998 EMBO J. 17:6230-6240; Lipford et al., 1998 Trends in Microbiol. 6:496-500). However, it is now clear that mouse lymphocytes respond quite well to phosphodiester CpG motifs that do not follow this "formula" (Yi et al., 1998 J. Immunol. 160:5898-5906) and the same is true of human B cells and dendritic cells (Hartmann et al., 1999 Proc. Natl. Acad. Sci. USA 96:9305-10; Liang, 1996 J. Clin. Invest. 98:1119-1129).

A variety of modifications to the phosphodiester backbone of immunostimulatory oligonucleotides have been made. Modifications at phosphorus have included neutral as well as positively and negatively charged species such as phosphorothioate (PS) species. PS oligonucleotides show good immune stimulatory activity which is only superseded by the semi-soft ODNs, in which the internucleotide linkage at CpG is a phosphodiester (PO) linkage. It is generally assumed that the substituents at the phosphorous atom must have similar charge and size to obtain comparable activity.

SUMMARY

The invention relates to an oligonucleotide which comprises one or more modifications that elicit enhanced immunostimulatory capacity. In particular, the invention is based on the finding that oligonucleotides having at least one pyrimidine-purine (Py-Pu) motif corresponding to formula I (below) are highly effective in mediating an immune response. These oligonucleotides are useful therapeutically and prophylactically for inducing an immune response and for treating diseases and disorders such as cancer and viral infections.

In one aspect, the invention is a composition comprising an immunostimulatory oligonucleotide having at least one modified pyrimidine-purine dinucleotide according to Formula I:

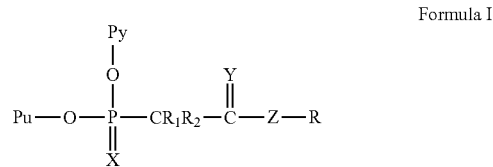

Formula I wherein R is hydrogen (H), C1-C4-alkyl, methoxyethyl, pivaloyl oxymethyl, pivaloyl oxybenzyl, or S-pivaloyl thioethyl or a physiologically tolerated salt thereof; X, Y and Z are oxygen (O) or sulfur (S); R1 and R2 are H or C1-C4 alkyl; Py is a nucleoside or nucleoside analog with a pyrimidine base Pu is a nucleoside or nucleoside analog with a purine base.

In some embodiments, the immunostimulatory oligonucleotide further comprises a second pyrimidine-purine dinucleotide, where the second pyrimidine-purine dinucleotide has a phosphorothioate linkage. In another embodiment the immunostimulatory oligonucleotide further comprises at least a second pyrimidine-purine dinucleotide, wherein the second pyrimidine-purine dinucleotide has a phosphodiester linkage. In yet another embodiment, the immunostimulatory oligonucleotide further comprises at least a second pyrimidine-purine dinucleotide, wherein the second pyrimidine-purine dinucleotide has a phosphorothioate linkage and further comprising at least a third pyrimidine-purine dinucleotide, wherein the third pyrimidine-purine dinucleotide has a phosphodiester linkage.

In some embodiments at least one nucleotide of the immunostimulatory oligonucleotide has a modified sugar residue selected from the group consisting essentially of 2'-fluoro-2'-deoxyribose, 2'-amino-2' deoxyribose, 2'-O-alkyl-ribose, or 3'-O-alkyl-ribose. In some embodiments the immunostimulatory oligonucleotide contains at least one internucleotide linkage selected from the group consisting of 2'-5', 5'-5',3'-3', 2'-2', or 2'-3' linkages. In some embodiments the immunostimulatory oligonucleotide is a B class, C class, P class, T class, or E class oligonucleotide.

In some embodiments the composition further comprises an antibacterial agent, an anticancer agent, an antiviral agent, an asthma or allergy medicament, or an autoimmune disease medicament. In another embodiment the immunostimulatory oligonucleotide is a TLR9 ligand. In another embodiment one or more of the pyrimidine-purine dinucleotides is a C-G dinucleotide. In one embodiment the second pyrimidine-purine dinucleotide is a C-G dinucleotide. In another embodiment the first pyrimidine-purine dinucleotide is a C-G dinucleotide. In yet another embodiment the immunostimulatory oligonucleotide includes at least two C-G dinucleotides. In still another embodiment the immunostimulatory oligonucleotide includes at least three C-G dinucleotides. In one embodiment the immunostimulatory oligonucleotide includes at least one phosphorothioate internucleotide linkage. In another embodiment the immunostimulatory oligonucleotide includes at least one phosphodiester internucleotide linkage. In some embodiments the immunostimulatory oligonucleotide is formulated with an antigen.

Another aspect of the invention provides a method of stimulating an immune response in a subject, comprising administering to a subject an effective amount for stimulating an immune response of a composition comprising an immunostimulatory oligonucleotide having at least one phosphonoacetate-like internucleotide linkage, wherein the oligonucleotide backbone is chimeric, and a pharmaceutical carrier. In one embodiment, the subject has a bacterial infection and the composition is administered in an effective amount for treating the bacterial infection. In another embodiment, the subject has an allergy and the composition is administered in an effective amount for treating the allergy. In yet another embodiment, the composition is administered in an effective amount for treating asthma. In still another embodiment the subject has an autoimmune disease and the composition is administered in an effective amount for treating the autoimmune disease.

In one embodiment the immunostimulatory oligonucleotide is any one or more of the immunostimulatory oligonucleotide described herein. In particular embodiments the immunostimulatory oligonucleotide is not an antisense, ribozyme or aptamer. In one embodiment the immunostimulatory oligonucleotide is formulated with an antigen.

Another aspect of the invention provides a method of treating cancer in a subject, comprising administering to the subject in need of such treatment a composition comprising any one or more of the immunostimulatory oligonucleotide described herein in an effective amount for treating cancer, and a pharmaceutical carrier. In one embodiment, the oligonucleotide is delivered by a route selected from the group consisting of oral, nasal, sublingual, intravenous, subcutaneous, mucosal, respiratory, direct injection, and dermally. In another embodiment, a therapeutic protocol is administered to the subject. In one embodiment the therapeutic protocol is surgery. In another embodiment the therapeutic protocol is radiation. In still another embodiment the therapeutic protocol is a medicament. In yet another embodiment the oligonucleotide is formulated. In another embodiment the oligonucleotide is associated with a targeting molecule.

Another aspect of the invention provides a method of treating an infection in a subject, comprising administering to the subject in need of such treatment a composition comprising any one or more of the immunostimulatory oligonucleotide described herein in an effective amount for treating the infection, and a pharmaceutical carrier. In one embodiment the oligonucleotide is delivered by a route selected from the group consisting of oral, nasal, sublingual, intravenous, subcutaneous, mucosal, respiratory, direct injection, and dermal. In one embodiment the infectious disease is a bacterial infection. In another embodiment the infection is a viral infection. In yet another embodiment the infection is a parasitic infection. In another embodiment the infection is a fungal infection.

In one embodiment the oligonucleotide is an A class oligonucleotide. In another embodiment the oligonucleotide is B class immunostimulatory oligonucleotide. In yet another embodiment the oligonucleotide is C class immunostimulatory oligonucleotide. In still another embodiment the oligonucleotide is P class immunostimulatory oligonucleotide. In another embodiment the oligonucleotide is T class immunostimulatory oligonucleotide. In yet another embodiment the oligonucleotide is E class immunostimulatory oligonucleotide. In one embodiment the oligonucleotide is a DNA/RNA hybrid, and the oligonucleotide comprises a CG dinucleotide with a phosphodiester linkage.

Another aspect of the invention provides a method of treating asthma in a subject, comprising administering to the subject in need of such treatment a composition comprising an immunostimulatory oligonucleotide having at least one phosphonoacetate-like internucleotide linkage, wherein the oligonucleotide backbone is chimeric in an effective amount for treating asthma, and a pharmaceutical carrier. In some embodiments the immunostimulatory oligonucleotide is a B class, C class, P class, T class, or E class oligonucleotide. In another embodiment the oligonucleotide is a DNA/RNA hybrid, and the internucleotide linkage at the CG dinucleotide is a phosphodiester linkage. In another embodiment, the oligonucleotide is delivered by a route selected from the group consisting of oral, nasal, sublingual, intravenous, subcutaneous, mucosal, respiratory, direct injection, and dermal.

Another aspect of the invention provides a method of treating allergy in a subject, comprising administering to the subject in need of such treatment a composition comprising an immunostimulatory oligonucleotide having at least one phosphonoacetate-like internucleotide linkage, wherein the oligonucleotide backbone is chimeric in an effective amount for treating allergy, and a pharmaceutical carrier. In some embodiments the immunostimulatory oligonucleotide is a B class, C class, P class, T class, or E class oligonucleotide. In another embodiment the oligonucleotide is a DNA/RNA hybrid, and the internucleotide linkage at the CG dinucleotide is a phosphodiester linkage. In another embodiment, the oligonucleotide is delivered by a route selected from the group consisting of oral, nasal, sublingual, intravenous, subcutaneous, mucosal, respiratory, direct injection, and dermal.

Another aspect of the invention is a composition comprising an immunostimulatory oligonucleotide having at least one phosphonoacetate-like linkage, wherein the oligonucleotide backbone is chimeric and the oligonucleotide is linked to at least one therapeutic agent. In one embodiment the therapeutic agent is a second oligonucleotide and the second oligonucleotide is linked to the immunostimulatory oligonucleotide to form a branched structure. In another embodiment the therapeutic agent is a second oligonucleotide and the second oligonucleotide is linked to the immunostimulatory oligonucleotide to form a 3'-3' linkage. In yet another embodiment the therapeutic agent is a second oligonucleotide and the second oligonucleotide and the immunostimulatory oligonucleotide form dendrimers. In still another embodiment the therapeutic agent is an anti-viral agent. In another embodiment the therapeutic agent is an anti-cancer agent. In one embodiment the linkage between the oligonucleotide and the therapeutic agent is covalent. In one embodiment the linkage between the oligonucleotide and the therapeutic agent is non-covalent. In one embodiment the composition comprises an antigen.

Use of an oligonucleotide of the invention for stimulating an immune response is also provided as an aspect of the invention.

A method for manufacturing a medicament of an oligonucleotide of the invention for stimulating an immune response is also provided.

Each of the limitations of the invention can encompass various embodiments of the invention. It is, therefore, anticipated that each of the limitations of the invention is involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF THE DRAWINGS

The figures are illustrative only and are not required for enablement of the invention disclosed herein.

FIG. 3 is three graphs showing TLR9 stimulation in TLR9-transfected HEK 293 cells following stimulation with B class ODN, as measured by luciferase assay.

FIG. 5 is three graphs showing TLR9 stimulation in TLR9-transfected HEK 293 cells following stimulation with ODN comprising multiple CpG motifs.

DETAILED DESCRIPTION

Figure 1:
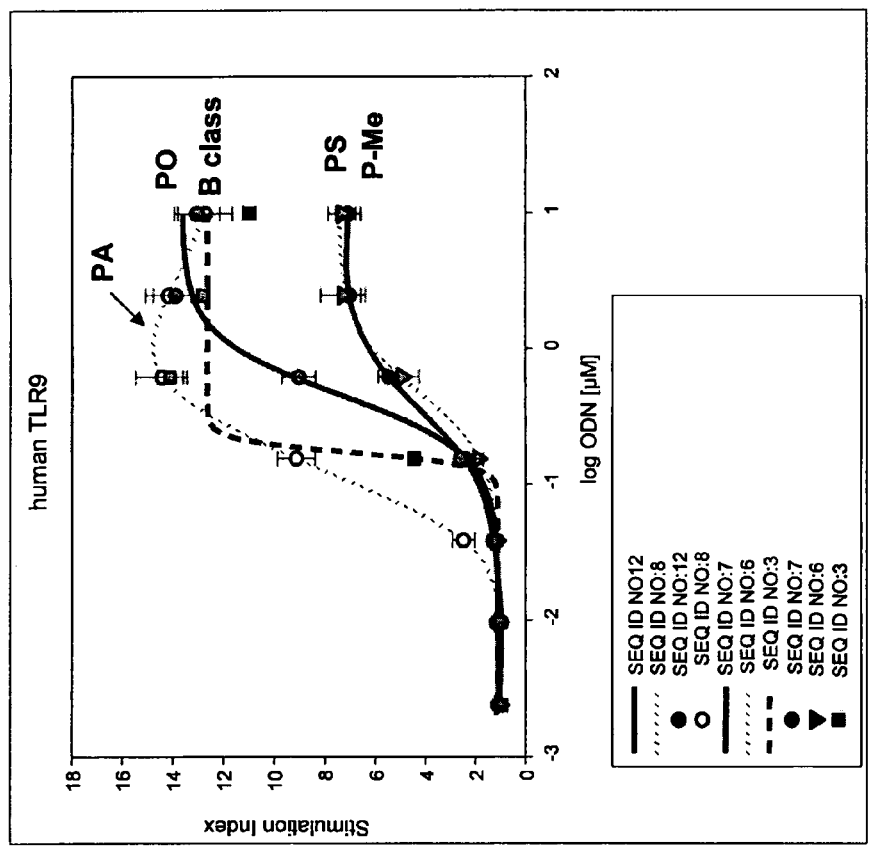
FIG. 1 is a graph showing a comparison of B class oligonucleotides (ODN) with identical sequence and phosphodiester (PO) (SEQ ID NO:7, red line), phosphorothioate (PS) (SEQ ID NO:3, red dotted line), methylphosphonate (P-Me) (SEQ ID NO:12, black line), or phosphonoacetate (PA) (SEQ ID NO:8, black dotted line) backbone modifications. The figure shows that the ODN with the PA modification induced human TLR9 activity in TLR9-transfected HEK 293 cells to a greater extent at lower ODN concentration compared to the other backbone modifications, as measured by luciferase assay. The y-axis is stimulation index and the x-axis is the log of ODN concentration in μM.

The invention is based in part on the discovery of a type of stabilized oligonucleotide that shows enhanced immunostimulatory capacity. Modifications of the oligonucleotide backbone, such as phosphorothioate modifications, often result in oligonucleotides with increased stability. In some instances backbone modification may result in reduced capacity to stimulate TLR9 activity, thus sacrificing some of the potency of non-stabilized oligonucleotides. It was discovered by the inventors that immunostimulatory oligonucleotides with a specific modification of the backbone have not only increased stability but also enhanced ability to stimulate interferon-α (IFN-α) production and induce TLR9 activation. As a result, these molecules have enhanced potency.

The invention relates generally to immunostimulatory oligonucleotides that contain certain backbone modifications, as well as to related immunostimulatory oligonucleotides and compositions. The immunostimulatory oligonucleotides of the invention are useful in any setting or application that calls for a composition or method for stimulating or augmenting an immune response. The oligonucleotides of the invention are of particular use in the preparation of pharmaceutical compositions, including adjuvants, vaccines, and other medicaments for use in treating a variety of conditions, including cancer, infectious disease, allergy, and asthma, inflammatory and autoimmune disease. The invention in certain aspects thus relates to immunostimulatory compositions that include immunostimulatory oligonucleotides of the invention, as well as methods of their use. Also as disclosed below, the oligonucleotides of the invention are of particular use in methods for activating an immune cell, vaccinating a subject, treating a subject having or at risk of having an immune system deficiency, an infection, cancer, an allergic condition, or inflammatory or autoimmune disease.

The immunostimulatory oligonucleotides of the invention comprise pyrimidine-purine (Py-Pu) dinucleotides described by Formula I:

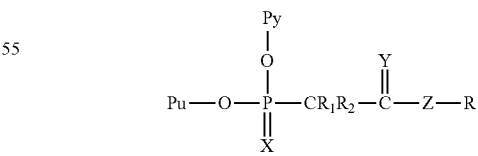

where R is hydrogen (H), C1-C4-alkyl, methoxyethyl, pivaloyl oxymethyl, pivaloyl oxybenzyl, or S-pivaloyl thioethyl or a physiologically tolerated salt thereof; X, Y and Z are oxygen (O) or sulfur (S); R1 and R2 are H or C1-C4 alkyl; Py is a nucleoside or nucleoside analog with a pyrimidine base and Pu is a nucleoside or nucleoside analog with a purine base.

The term "immunostimulatory oligonucleotide," or equivalently, "immunostimulatory nucleic acid" in the context of this invention refers to any nucleic acid that has at least one Py-Pu immunostimulatory dinucleotide of the invention and is capable of activating an immune cell. In some embodiments of the invention the pyrimidine-purine dinucleotide may be a CpG dinucleotide. In such a case, at least the C of the CpG dinucleotide is typically, but not necessarily, unmethylated. Immunostimulatory nucleic acids comprising pyrimidine-purine dinucleotides are described in a number of issued patents and published patent applications, including U.S. Pat. Nos. 6,194,388; 6,207,646; 6,218,371; 6,239,116; 6,339,068; 6,406,705; and 6,429,199. In some aspects of the invention it is desirable that the immunostimulatory oligonucleotides have more than one Py-Pu immunostimulatory dinucleotide.

An immunostimulatory oligonucleotide containing at least one Py-Pu dinucleotide is a nucleic acid molecule which contains a pyrimidine-purine dinucleotide sequence corresponding to formula I and which activates the immune system. A non-limiting example of an immunostimulatory nucleic acid containing at least one at least one Py-Pu dinucleotide is a nucleic acid which contains an unmethylated cytosine-guanine dinucleotide sequence (i.e., an unmethylated 5' cytidine followed by a 3' guanosine and linked by a phosphonoacetate or phosphonoacetate-like bond). In some aspects of the invention the Py-Pu dinucleotide is a C-G dinucleotide. A "C-G" dinucleotide is described as a dinucleotide according to the formula 5'-Py-Pu-3', wherein Py is C or a modified C and Pu is G or a modified G. The immunostimulatory oligonucleotides of the instant invention may contain multiple C-G dinucleotides. One or more of the C-G dinucleotides may have a phosphonoacetate or phosphonoacetate-like internucleotide linkage.

In some embodiments the immunostimulatory oligonucleotides act as TLR9 ligands. As used herein, the term "TLR9 ligand" refers to any agent that is capable of inducing an increase in TLR9 signaling (i.e., an agonist of TLR9). TLR9 ligands specifically include, without limitation, immunostimulatory CpG nucleic acid molecules.

In some aspects of the invention the immunostimulatory oligonucleotides contain phosphonoacetate or phosphonoacetate-like internucleotide linkages. In some embodiments the linkages occur only within at least one internal Py-Pu dinucleotide. In other embodiments the linkages occur within multiple Py-Pu dinucleotides or in less than all the Py-Pu dinucleotides. It is also possible in the context of the invention for phosphonoacetate or phosphonoacetate-like internucleotide linkages to occur outside the Py-Pu immunostimulatory dinucleotide. Phosphonoacetate and phosphonoacetate-like linkages are described by formula I and by the formulae below:

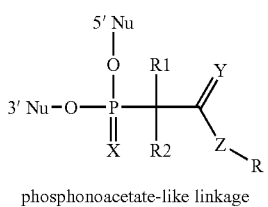

phosphonoacetate-like linkage

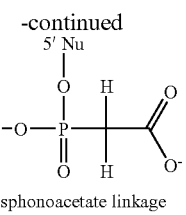

phosphonoacetate linkage wherein R, R1, R2, Y, and Z are defined as described above, and Nu is any nucleotide.

The immunostimulatory oligonucleotides may have further backbone modifications in addition to the phosphonoacetate or phosphonoacetate-like linkage at the Py-Pu dinucleotide. A stabilized internucleotide linkage is an internucleotide linkage that is relatively resistant to in vivo degradation (e.g., via an exo- or endo-nuclease), compared to a phosphodiester internucleotide linkage. In addition to the phosphonoacetate, and phosphonoacetate-like linkages, the oligonucleotides may contain other stabilized internucleotide linkages, including, without limitation, phosphorothioate, phosphorodithioate, methylphosphonate, and methylphosphorothioate. Other stabilized internucleotide linkages include, without limitation: peptide, alkyl, and dephospho. Phosphonoacetate internucleotide linkages, like other stabilized linkages, have reduced susceptibility to nuclease digestion and increased ability to activate RNAse H. Thus for example phosphodiester, but not phosphonoacetate, oligonucleotides are susceptible to nuclease digestion, while both phosphodiester and phosphonoacetate oligonucleotides activate RNAse H. In some embodiments, the Py-Pu immunostimulatory oligonucleotide includes at least one phosphodiester internucleotide linkage.

The immunostimulatory oligonucleotides may include, in addition to the phosphonoacetate or phosphonoacetate-like internucleotide linkages at preferred internal positions, 5' and 3' ends that are resistant to degradation. Such degradation-resistant ends can involve any suitable modification that results in an increased resistance against exonuclease digestion over corresponding unmodified ends. For instance, the 5' and 3' ends can be stabilized by the inclusion there of at least one phosphate modification of the backbone. In one embodiment, the at least one phosphate modification of the backbone at each end is independently a phosphorothioate, phosphorodithioate, phosphonoacetate, phosphonoacetate-like, methylphosphonate, or methylphosphorothioate internucleotide linkage. In another embodiment, the degradation-resistant end includes one or more nucleotide units connected by peptide or amide linkages at the 3' end.

The terms "nucleic acid" and "oligonucleotide" also encompass nucleic acids or oligonucleotides with substitutions or modifications, such as in the bases and/or sugars. For example, they include nucleic acids having backbone sugars that are covalently attached to low molecular weight organic groups other than a hydroxyl group at the 2' position and other than a phosphate group or hydroxy group at the 5' position. Thus modified nucleic acids may include a 2'-O-alkylated deoxyribose group. In addition, modified nucleic acids may include sugars such as arabinose or 2'-fluoroarabinose instead of deoxyribose. Thus the nucleic acids may be heterogeneous in backbone composition thereby containing any possible combination of polymer units linked together such as peptide-nucleic acids (which have an amino acid backbone with nucleic acid bases). In the context of the instant invention, the oligonucleotides are not antisense oligonucleotides, ribozymes, or aptamers.

Nucleic acids also include substituted purines and pyrimidines such as C-5 propyne pyrimidine and 7-deaza-7-substituted purine modified bases (Wagner R W et al., (1996) *Nat Biotechnol* 14:840-4). Purines and pyrimidines include but are not limited to adenine, cytosine, guanine, thymine, 5-methylcytosine, 5-hydroxycytosine, 5-fluorocytosine, 2-aminopurine, 2-amino-6-chloropurine, 2,6-diaminopurine, hypoxanthine, and other naturally and non-naturally occurring nucleobases, substituted and unsubstituted aromatic moieties. Other such modifications are well known to those of skill in the art.

The immunostimulatory oligonucleotides of the invention may include motifs and properties of other ODN classes such, as A class, B class, C class, T class, P class and E class as long as they include modified pyrimidine-purine dinucleotide according to Formula I. "B class" ODN are potent at activating B cells but are relatively weak in inducing IFN-α and NK cell activation. The B class CpG nucleic acids typically are fully stabilized and include an unmethylated CpG dinucleotide within certain preferred base contexts. See, e.g., U.S. Pat. Nos. 6,194,388; 6,207,646; 6,214,806; 6,218,371; 6,239,116; and 6,339,068. Another class is potent for inducing IFN-α and NK cell activation but is relatively weak at stimulating B cells; this class has been termed the A class. The "A class" CpG nucleic acids typically have stabilized poly-G sequences at 5' and 3' ends and a palindromic phosphodiester CpG dinucleotide-containing sequence of at least 6 nucleotides. See, for example, published patent application PCT/US00/26527 (WO 01/22990). Yet another class of CpG nucleic acids activates B cells and NK cells and induces IFN-α; this class has been termed the "C class." The C class CpG nucleic acids, as first characterized, typically are fully stabilized, include a B class-type sequence and a GC-rich palindrome or near-palindrome. This class has been described in U.S. provisional patent application 60/313,273, filed Aug. 17, 2001, U.S. Ser. No. 10/224,523 filed on Aug. 19, 2002, and US the entire contents of which are incorporated herein by reference. These combination motif nucleic acids have immune stimulating effects that fall somewhere between those effects associated with traditional B class CpG ODN, which are strong inducers of B cell activation and dendritic cell (DC) activation, and those effects associated with a more recently described class of immune stimulatory nucleic acids (B class CpG ODN) which are strong inducers of IFN-α and natural killer (NK) cell activation but relatively poor inducers of B-cell and DC activation. Krieg A M et al., (1995) *Nature* 374:546-9; Ballas Z K et al., (1996) *J Immunol* 157:1840-5; Yamamoto S et al., (1992) *J Immunol* 148:4072-6. While prior art B class CpG ODN often have phosphorothioate backbones and prior art A class CpG ODN have mixed or chimeric backbones, the C class of combination motif immune stimulatory nucleic acids may have either stabilized, e.g., phosphorothioate, chimeric, or phosphodiester backbones, and in some cases they have semi-soft backbones. The phosphonate or phosphonate-like modifications can be incorporated into each of these types of molecules.

The "T class" oligonucleotides induce secretion of lower levels of IFN-α when not modified as in the instant ODNs of the invention and IFN-related cytokines and chemokines than B class or C class oligonucleotides, while retaining the ability to induce levels of IL-10 similar to B class oligonucleotides. See e.g., U.S. patent application Ser. No. 11/099,683. Another class, the P class oligonucleotides, has the ability in some instances to induce much higher levels of IFN-α secretion than the C class. The "P Class" oligonucleotides have the ability to spontaneously self-assemble into concatamers either in vitro and/or in vivo. Without being bound by any particular theory for the method of action of these molecules, one potential hypothesis is that this property endows the P Class oligonucleotides with the ability to more highly crosslink TLR9 inside certain immune cells, inducing a distinct pattern of immune activation compared to the previously described classes of CpG oligonucleotides. See e.g., U.S. patent application Ser. No. 11/706,561. The "E class" oligonucleotides are a subclass of the A, B, C, T, or P class oligonucleotides that further comprise the sequence $R_3$Py-Pu $R_4$, wherein $R_3$ and $R_4$ are each a lipophilic substituted nucleotide analog, wherein Py is a pyrimidine nucleotide and wherein Pu is a purine or an abasic residue. Preferred lipophilic nucleotide analogs are e.g., 5-chloro-uracil, 5-bromo-uracil, 5-iodo-uracil, 5-ethyl-uracil, 5-propyl-uracil, 2.4-difluorotoluene, and 3-nitropyrrole.

Modified backbones such as those with phosphonoacetate or phosphonoacetate-like linkages and others may be synthesized using automated techniques employing either phosphoramidate or H-phosphonate chemistries. Synthesis is described e.g., in international patent application WO 02/32912. Synthesis of oligonucleotides with phosphonoacetate and phosphonoacetate-like linkages is described for example in U.S. Pat. No. 6,693,187, the contents of which are herein incorporated by reference. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (Uhlmann, E. et al., (1990) *Chem Rev* 90:544; Goodchild, J. (1990) *Bioconjugate Chem* 1:165). Methods for preparing chimeric oligonucleotides are also known. For instance patents issued to Uhlmann et al., have described such techniques.

The oligonucleotides may be DNA or RNA. In one embodiment the immunostimulatory oligonucleotides of the invention are DNA/RNA hybrid molecules comprising a mixed backbone of ribose and deoxyribose. DNA/RNA hybrid oligonucleotides often demonstrate increased activities in a variety of T cell-dependent applications and stimulation with these oligonucleotides often results in induction of a different profile of immune response-associated molecules such as cytokines. In one embodiment these DNA/RNA hybrid oligonucleotides are single-stranded. In another embodiment all or part of the oligonucleotide is double-stranded.

In one embodiment the immunostimulatory oligonucleotides of the invention are in the form of covalently closed, dumbbell-shaped molecules with both primary and secondary structure. In one embodiment such cyclic oligoribonucleotides include two single-stranded loops connected by an intervening double-stranded segment. In one embodiment at least one single-stranded loop includes an immunostimulatory DNA motif of the invention. Other covalently closed, dumbbell-shaped molecules of the invention include chimeric DNA/RNA molecules in which, for example, the double-stranded segment is at least partially DNA (e.g., either homodimeric dsDNA or heterodimeric DNA:RNA) and at least one single-stranded loop includes an immunostimulatory DNA motif of the invention. Alternatively, the double stranded segment of the chimeric molecule is DNA.

The immunostimulatory oligonucleotides of the invention can also include other modifications. These include nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

The immunostimulatory oligonucleotides of the instant invention can encompass various chemical modifications and substitutions, in comparison to natural RNA and DNA, involving a phosphodiester internucleotide bridge, a β-D-ribose unit and/or a natural nucleotide base (adenine, guanine, cytosine, thymine, uracil). Examples of chemical modifications are known to the skilled person and are described, for example, in Uhlmann, E. et al., (1990) *Chem Rev* 90:543; "Protocols for Oligonucleotides and Analogs" Synthesis and Properties & Synthesis and Analytical Techniques, S. Agrawal, Ed, Humana Press, Totowa, USA 1993; Crooke, S. T. et al., (1996) *Annu Rev Pharmacol Toxicol* 36:107-129; and Hunziker, J. et al., (1995) *Mod Synth Methods* 7:331-417. An oligonucleotide according to the invention may have one or more modifications, wherein each modification is located at a particular phosphodiester internucleotide bridge and/or at a particular β-D-ribose unit and/or at a particular natural nucleotide base position in comparison to an oligonucleotide of the same sequence which is composed of natural DNA or RNA.

For example, the invention relates to an oligonucleotide which may comprise one or more modifications and wherein each modification is independently selected from:
a) the replacement of a phosphodiester internucleotide bridge located at the 3' and/or the 5' end of a nucleotide by a modified internucleotide bridge,
b) the replacement of phosphodiester bridge located at the 3' and/or the 5' end of a nucleotide by a dephospho bridge,
c) the replacement of a sugar phosphate unit from the sugar phosphate backbone by another unit,
d) the replacement of a β-D-ribose unit by a modified sugar unit, and
e) the replacement of a natural nucleotide base by a modified nucleotide base.

More detailed examples for the chemical modification of an oligonucleotide are as follows.

A phosphodiester internucleotide bridge located at the 3' and/or the 5' end of a nucleotide can be replaced by a modified internucleotide bridge, wherein the modified internucleotide bridge is for example selected from phosphorothioate, phosphorodithioate, $NR^1R^2$-phosphoramidate, boranophosphate, α-hydroxybenzyl phosphonate, phosphate-$(C_1$-$C_{21})$—O-alkyl ester, phosphate-$[(C_6$-$C_{12})$aryl-$(C_1$-$C_{21})$—O-alkyl]ester, $(C_1$-$C_8)$alkylphosphonate and/or $(C_6$-$C_{12})$arylphosphonate bridges, $(C_7$-$C_{12})$-α-hydroxymethyl-aryl (e.g., disclosed in WO 95/01363), wherein $(C_6$-$C_{12})$aryl, $(C_6$-$C_{20})$aryl and $(C_6$-$C_{14})$aryl are optionally substituted by halogen, alkyl, alkoxy, nitro, cyano, and where $R^1$ and $R^2$ are, independently of each other, hydrogen, $(C_1$-$C_{18})$-alkyl, $(C_6$-$C_{20})$-aryl, $(C_6$-$C_{14})$-aryl-$(C_1$-$C_8)$-alkyl, preferably hydrogen, $(C_1$-$C_8)$-alkyl, preferably $(C_1$-$C_4)$-alkyl and/or methoxyethyl, or $R^1$ and $R^2$ form, together with the nitrogen atom carrying them, a 5-6-membered heterocyclic ring which can additionally contain a further heteroatom from the group O, S and N.

The replacement of a phosphodiester bridge located at the 3' and/or the 5' end of a nucleotide by a dephospho bridge (dephospho bridges are described, for example, in Uhlmann E and Peyman A in "Methods in Molecular Biology," Vol. 20, "Protocols for Oligonucleotides and Analogs," S. Agrawal, Ed., Humana Press, Totowa 1993, Chapter 16, pp. 355 ff), wherein a dephospho bridge is for example selected from the dephospho bridges formacetal, 3'-thioformacetal, methylhydroxylamine, oxime, methylenedimethyl-hydrazo, dimethylenesulfone and/or silyl groups.

A sugar phosphate unit (i.e., a β-D-ribose and phosphodiester internucleotide bridge together forming a sugar phosphate unit) from the sugar phosphate backbone (i.e., a sugar phosphate backbone is composed of sugar phosphate units) can be replaced by another unit, wherein the other unit is for example suitable to build up a "morpholino-derivative" oligomer (as described, for example, in Stirchak E P et al., (1989) *Nucleic Acids Res* 17:6129-41), that is, e.g., the replacement by a morpholino-derivative unit; or to build up a polyamide nucleic acid ("PNA"; as described for example, in Nielsen P E et al., (1994) *Bioconjug Chem* 5:3-7), that is, e.g., the replacement by a PNA backbone unit, e.g., by 2-aminoethylglycine.

A β-D-ribose unit or a β-D-2'-deoxyribose unit can be replaced by a modified sugar unit, wherein the modified sugar unit is for example selected from α-D-2'-deoxyribose, α-L-2'-deoxyribose, β-L-2'-deoxyribose, β-L-ribose, 2'-F-2'-deoxyribose, 2'-F-2'-deoxy-arabinose, 2'-O—$(C_1$-$C_6)$alkyl-ribose, preferably 2'-O—$(C_1$-$C_6)$alkyl-ribose is 2'-O-methylribose, 2'-O—$(C_2$-$C_6)$alkenyl-ribose, 2'-[O—$(C_1$-$C_6)$alkyl-O—$(C_1$-$C_6)$alkyl]-ribose, 2'—$NH_2$-2'-deoxyribose, β-D-xylo-furanose, α-arabinofuranose, 2,4-dideoxy-β-D-erythro-hexo-pyranose, and carbocyclic (described, for example, in Froehler, J. (1992) *Am Chem Soc* 114:8320) and/or open-chain sugar analogs (described, for example, in Vandendriessche et al., (1993) *Tetrahedron* 49:7223) and/or bicyclosugar analogs (described, for example, in Tarkov, M. et al., (1993) *Helv Chim Acta* 76:481).

In some embodiments the sugar is 2'-O-methylribose, 2'-deoxyribose, 2'-fluoro-2'-deoxyribose, 2'-amino-2' deoxyribose, 2'-O-alkyl-ribose, or 3'-O-alkyl-ribose and/or 2'-O-4'-C-alkylene ribose, such as 2'-O-4'-C-methylene ribose (also called LNA).

Nucleic acids also include substituted purines and pyrimidines such as C-5 propyne pyrimidine and 7-deaza-7-substituted purine modified bases (Wagner, R. W. et al., (1996) *Nat Biotechnol* 14:840-4). Purines and pyrimidines include but are not limited to adenine, cytosine, guanine, and thymine, and other naturally and non-naturally occurring nucleobases, substituted and unsubstituted aromatic moieties.

A modified base is any base which is chemically distinct from the naturally occurring bases typically found in DNA and RNA such as T, C, G, A, and U, but which share basic chemical structures with these naturally occurring bases. The modified nucleotide base may be, for example, selected from hypoxanthine, uracil, dihydrouracil, pseudouracil, 2-thiouracil, 4-thiouracil, 5-aminouracil, 5-$(C_1$-$C_6)$-alkyluracil, 5-$(C_2$-$C_6)$-alkenyluracil, 5-$(C_2$-$C_6)$-alkynyluracil, 5-(hydroxymethyl)uracil, 5-chlorouracil, 5-fluorouracil, 5-bromouracil, 5-iodo-uracil, 2.4-difluoro-toluene, and 3-nitropyrrole, 5-hydroxycytosine, 5-$(C_1$-$C_6)$-alkylcytosine, 5-$(C_2$-$C_6)$-alkenylcytosine, 5-$(C_2$-$C_6)$-alkynylcytosine, 5-chlorocytosine, 5-fluorocytosine, 5-bromocytosine, $N^2$-dimethylguanine, 2,4-diamino-purine, 8-azapurine, a substituted 7-deazapurine, preferably 7-deaza-7-substituted and/or 7-deaza-8-substituted purine, 5-hydroxymethylcytosine, N4-alkylcytosine, e.g., N4-ethylcytosine, 5-hydroxydeoxycytidine, 5-hydroxymethyldeoxycytidine, N4-alkyldeoxycytidine, e.g., N4-ethyldeoxycytidine, 6-thiodeoxyguanosine, and deoxyribonucleotides of nitropyrrole, C5-propynylpyrimidine, and diaminopurine e.g., 2,6-diaminopurine, inosine, 5-methylcytosine, 2-aminopurine, 2-amino-6-chloropurine, hypoxanthine or other modifications of a natural nucleotide bases. This list is meant to be exemplary and is not to be interpreted to be limiting.

Herein "Py" is used to refer to pyrimidine and in some embodiments a nucleotide containing a cytosine or a modified cytosine. A modified cytosine as used herein is a naturally occurring or non-naturally occurring pyrimidine base analog of cytosine which can replace this base without impairing the immunostimulatory activity of the oligonucleotide. Modified cytosines include but are not limited to 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil). Some of the preferred cytosines include 5-methyl-cytosine, 5-fluoro-cytosine, 5-hydroxy-cytosine, 5-hydroxymethyl-cytosine, and N4-ethyl-cytosine. In another embodiment of the invention, the cytosine base is substituted by a universal base (e.g., 3-nitropyrrole, P-base), an aromatic ring system (e.g., fluorobenzene or difluorobenzene) or a hydrogen atom (dSpacer).

Herein "Pu" is used to refer to a purine or modified purine. In some embodiments Pu is a guanine or a modified guanine base. A modified guanine as used herein is a naturally occurring or non-naturally occurring purine base analog of guanine which can replace this base without impairing the immunostimulatory activity of the oligonucleotide. Modified guanines include but are not limited to 7-deazaguanine, 7-deaza-7-substituted guanine (such as 7-deaza-7-(C2-C6) alkynylguanine), 7-deaza-8-substituted guanine, hypoxanthine, N2-substituted guanines (e.g., N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g., N6-methyl-adenine, 8-hydroxyadenine) 8-substituted guanine (e.g., 8-hydroxyguanine and 8-bromoguanine), and 6-thioguanine. In another embodiment of the invention, the guanine base is substituted by a universal base (e.g., 4-methyl-indole, 5-nitro-indole, and K-base), an aromatic ring system (e.g., benzimidazole or dichloro-benzimidazole, 1-methyl-1H-[1,2,4]triazole-3-carboxylic acid amide) or a hydrogen atom (dSpacer).

The invention also encompasses oligonucleotides having unusual internucleotide linkages, including 5'-5', 2'-2',2'-3', and 2'-5' internucleotide linkages. In some aspects of the invention it is advantageous for the oligonucleotides to have one or more accessible 5' ends. It is possible to create modified oligonucleotides having two such 5' ends. This may be achieved, for instance by attaching two oligonucleotides through a 3'-3' linkage to generate an oligonucleotide having one or two accessible 5' ends. The 3'-3' linkage may be a phosphodiester, phosphorothioate, phosphonoacetate or any other modified internucleotide bridge. Methods for accomplishing such linkages are known in the art. For instance, such linkages have been described in Seliger, H. et al. Oligonucleotide analogs with terminal 3'-3'- and 5'-5'-internucleotidic linkages as antisense inhibitors of viral gene expression, Nucleotides & Nucleotides (1991), 10 (1-3), 469-77 and Jiang et al., Pseudo-cyclic oligonucleotides: in vitro and in vivo properties, Bioorganic & Medicinal Chemistry (1999), 7(12), 2727-2735.

In one embodiment such unusual linkages are excluded from the immunostimulatory DNA motif, even though one or more of such linkages may occur elsewhere within the polymer. For polymers having free ends, inclusion of one 3'-3' internucleotide linkage can result in a polymer having two free 5' ends. Conversely, for polymers having free ends, inclusion of one 5'-5' internucleotide linkage can result in a polymer having two free 3' ends.

Additionally, 3'3'-, 5'-5'-, 2'-2'-, 2'-3'-, and 2'-5'-linked nucleic acids where the linkage is not a phosphodiester, phosphorothioate, phosphonoacetate or other modified bridge, can be prepared using an additional spacer, such as tri- or tetra-ethylenglycol phosphate moiety (Durand, M. et al., Triple-helix formation by an oligonucleotide containing one (dA)12 and two (dT)12 sequences bridged by two hexaethylene glycol chains, Biochemistry (1992), 31(38), 9197-204, U.S. Pat. No. 5,658,738, and U.S. Pat. No. 5,668,265). Alternatively, the non-nucleotidic linker may be derived from ethanediol, propanediol, or from an abasic deoxyribose (dSpacer) unit (Fontanel, Marie Laurence et al., Sterical recognition by T4 polynucleotide kinase of non-nucleosidic moieties 5'-attached to oligonucleotides; Nucleic Acids Research (1994), 22(11), 2022-7) using standard phosphoramidite chemistry. The non-nucleotidic linkers can be incorporated once or multiple times, or combined with each other allowing for any desirable distance between the 3'-ends of the two ODNs to be linked.

The oligonucleotide may contain a doubler or trebler unit (Glen Research, Sterling, Va.), in particular those modified oligodeoxyribonucleotide analogs with a 3'-3' linkage. A doubler unit in one embodiment can be based on 1,3-bis-[5-(4,4'-dimethoxytrityloxy)pentylamido]propyl-2-[(2-cyanoethyl)-(N,N-diisopropyl)]-phosphoramidite. A trebler unit in one embodiment can be based on incorporation of Tris-2,2, 2-[3-(4,4'-dimethoxytrityloxy)propyloxymethyl]ethyl-[(2-cyanoethyl)-(N,N-diisopropyl)]-phosphoramidite. Branching of the modified oligoribonucleotide analogs by multiple doubler, trebler, or other multiplier units leads to dendrimers which are a further embodiment of this invention. Branched modified oligoribonucleotide analogs may lead to crosslinking of receptors particularly for combinations of immunostimulatory RNA and DNA such as TLR3, TLR7, TLR8, and TLR9 with distinct immune effects compared to non-branched forms of the analogs. In addition, the synthesis of branched or otherwise multimeric analogs may stabilize DNA against degradation and may enable weak or partially effective DNA sequences to exert a therapeutically useful level of immune activity. The modified oligodeoxyribonucleotide analogs may also contain linker units resulting from peptide modifying reagents or oligonucleotide modifying reagents (Glen Research). Furthermore, the modified oligodeoxyribonucleotide analogs may contain one or more natural or unnatural amino acid residues which are connected to the polymer by peptide (amide) linkages.

The 3'-5', 5'-5',3'-3', 2'-2',2'-3', and 2'-5' internucleotide linkages can be direct or indirect. Direct linkages in this context refers to a phosphate or modified phosphate linkage as disclosed herein, without an intervening linker moiety. An intervening linker moiety is an organic moiety distinct from a phosphate or modified phosphate linkage as disclosed herein, which can include, for example, polyethylene glycol, triethylene glycol, hexaethylene glycol, dSpacer (i.e., an abasic deoxynucleotide), doubler unit, or trebler unit.

The linkages are preferably composed of C, H, N, O, S, B, P, and Halogen, containing 3 to 300 atoms. An example with 3 atoms is an acetal linkage (ODN1-3'-O—$CH_2$—O-3'-ODN2) connecting e.g., the 3'-hydroxy group of one nucleotide to the 3'-hydroxy group of a second oligonucleotide. An example with about 300 atoms is PEG-40 (tetraconta polyethyleneglycol). Preferred linkages are phosphodiester, to phosphorothioate, methylphosphonate, phosphoramidate, boranophosphonate, amide, ether, thioether, acetal, thioacetal, urea, thiourea, sulfonamide, Schiff Base and disulfide linkages. It is also possible to use the Solulink BioConjugation System i.e., (www.trilinkbiotech.com).

If the oligonucleotide is composed of two or more sequence parts, these parts can be identical or different. Thus, in an oligonucleotide with a 3'3'-linkage, the sequences can be identical 5'-ODN1-3'3'-ODN1-5' or different 5'-ODN1-3'3'-ODN2-5'. Furthermore, the chemical modification of the various oligonucleotide parts as well as the linker connecting them may be different. Since the uptake of short oligonucleotides appears to be less efficient than that of long oligonucleotides, linking of two or more short sequences results in improved immune stimulation. The length of the short oligonucleotides is preferably 2-20 nucleotides, more preferably 3-16 nucleotides, but most preferably 5-10 nucleotides. Preferred are linked oligonucleotides which have two or more unlinked 5'-ends.

The oligonucleotide partial sequences may also be linked by non-nucleotidic linkers. A "non-nucleotidic linker" as used herein refers to any linker element that is not a nucleotide or polymer thereof (i.e., a polynucleotide), wherein a nucleotide includes a purine or pyrimidine nucleobase and a sugar phosphate, in particular abasic linkers (dSpacers), triethylene glycol units or hexaethylene glycol units. Further preferred linkers are alkylamino linkers, such as C3, C6, C12 aminolinkers, and also alkylthiol linkers, such as C3 or C6 thiol linkers. The oligonucleotides can also be linked by aromatic residues which may be further substituted by alkyl or substituted alkyl groups.

For facilitating uptake into cells, the immunostimulatory oligonucleotides are in some embodiments in the range of 3 to 100 bases in length. In some embodiments the oligonucleotides are 7-100 bases in length. Typically, nucleic acids of any size greater than 6 nucleotides (even many kb long) are capable of inducing an immune response according to the invention if sufficient immunostimulatory motifs are present. However, the improved immunostimulatory capacity of the modified oligonucleotides of the invention provides for immunostimulatory molecules of much shorter length. In some embodiments the immunostimulatory oligonucleotides are 3-6 bases in length. The oligonucleotides may be longer than 100 nucleotides. For instance, they may be 120, 150, 200 or even longer in some circumstances.

Other stabilized oligonucleotides include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

The Py-Pu immunostimulatory oligonucleotides of the instant invention are useful for stimulating an immune response in a subject in need of such treatment. A subject in need of such treatment is a subject having or at risk of having an autoimmune disease or inflammatory condition, a subject having or at risk of having cancer, a cancer subject undergoing chemotherapy or radiation treatment, a subject having or at risk of contracting a viral, bacterial, or parasitic infection, a subject having asthma, a subject having allergy or allergic rhinitis, a subject having or at risk of having atherosclerosis, or a subject undergoing a tissue or organ transplant.

A subject at risk of developing a cancer is one who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. When a subject at risk of developing a cancer is treated with an antigen specific for the type of cancer to which the subject is at risk of developing and a PypPu immunostimulatory oligonucleotide, the subject may be able to kill the cancer cells as they develop. If a tumor begins to form in the subject, the subject will develop a specific immune response against the tumor antigen. A subject having a cancer is a subject that has detectable cancerous cells. The cancer may be a malignant or non-malignant cancer. "Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Hemopoietic cancers, such as leukemia, are able to outcompete the normal hemopoietic compartments in a subject, thereby leading to hemopoietic failure (in the form of anemia, thrombocytopenia and neutropenia) ultimately causing death. The subject may be treated with the Py-Pu oligonucleotide alone or in combination with antigen or other therapeutics.

A metastasis is a region of cancer cells, distinct from the primary tumor location, resulting from the dissemination of cancer cells from the primary tumor to other parts of the body. At the time of diagnosis of the primary tumor mass, the subject may be monitored for the presence of metastases. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Cancers include, but are not limited to, basal cell carcinoma, biliary tract cancer; bladder cancer; bone cancer; brain and central nervous system (CNS) cancer; breast cancer; cervical cancer; choriocarcinoma; colon and rectum cancer; connective tissue cancer; cancer of the digestive system; endometrial cancer; esophageal cancer; eye cancer; cancer of the head and neck; intra-epithelial neoplasm; kidney cancer; larynx cancer; leukemia; liver cancer; lung cancer (e.g., small cell and non-small cell); lymphoma including Hodgkin's and Non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; sarcoma; skin cancer; stomach cancer; testicular cancer; thyroid cancer; uterine cancer; cancer of the urinary system, as well as other carcinomas, adenocarcinomas, and sarcomas.

A subject having an infection is a subject that has been exposed to an infectious pathogen and has acute or chronic detectable levels of the pathogen in the body. The Py-Pu immunostimulatory oligonucleotides can be used with or without an antigen to mount an antigen specific systemic or mucosal immune response that is capable of reducing the level of or eradicating the infectious pathogen. An infectious disease, as used herein, is a disease arising from the presence of a foreign microorganism in the body. It is particularly important to develop effective vaccine strategies and treatments to protect the body's mucosal surfaces, which are the primary site of pathogenic entry. A subject at risk of having an infection is a subject that may be expected to come in contact with a microorganism. Nonlimiting examples of such subjects are medical workers or those traveling to parts of the world where the incidence of infection by the microorganism is high.

A subject having an allergy is a subject that has an allergic reaction in response to an allergen. An allergy refers to acquired hypersensitivity to a substance (allergen). Allergic conditions include but are not limited to eczema, allergic rhinitis or coryza, hay fever, conjunctivitis, bronchial asthma, urticaria (hives) and food allergies, and other atopic conditions.

Allergies are generally caused by IgE antibody generation against harmless allergens. The cytokines that are induced by systemic or mucosal administration of CpG immunostimulatory oligonucleotides are predominantly of a class called Th1 (examples are IL-12, IP-10, IFN-α and IFN-γ) and these induce both humoral and cellular immune responses. The other major type of immune response, which is associated with the production of IL-4 and IL-5 cytokines, is termed a Th2 immune response. In general, it appears that allergic diseases are mediated by Th2 type immune responses. Based on the ability of the CpG immunostimulatory oligonucleotides to shift the immune response in a subject from a predominant Th2 (which is associated with production of IgE antibodies and allergy) to a balanced Th2/Th1 response (which is protective against allergic reactions), an effective dose for inducing an immune response of a CpG immunostimulatory oligonucleotide can be administered to a subject to treat or prevent asthma and allergy.

Thus, the Py-Pu immunostimulatory oligonucleotides have significant therapeutic utility in the treatment of allergic and non-allergic conditions such as asthma. Th2 cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-γ and IL-12, can suppress the formation of Th2 clones and production of Th2 cytokines. Asthma refers to a disorder of the respiratory system characterized by inflammation, narrowing of the airways and increased reactivity of the airways to inhaled agents. Asthma is frequently, although not exclusively associated with atopic or allergic symptoms.

The immunostimulatory oligonucleotides of the instant invention may be useful for treating conditions that involve an innate immune response or a Th1-like immune response, including inflammation, atopic dermatitis, acute and chronic allograft rejection, graft-versus-host disease (GvHD), certain autoimmune diseases, and sepsis. The invention can be used to treat such conditions in view of the selective inhibition of TLR signaling that can be achieved according to the invention.

Autoimmune diseases can be generally classified as antibody-mediated, T-cell mediated, or a combination of antibody-mediated and T-cell mediated. The adaptor ODN and TLR ligand combinations of the invention are believed to be useful for treating various types of autoimmunity involving antibody-mediated or T-cell mediated immunity, including insulin-dependent (type I) diabetes mellitus, rheumatoid arthritis, multiple sclerosis, systemic lupus erythematosus (SLE), and inflammatory bowel disease (i.e., Crohn's disease and ulcerative colitis). Animal models for these autoimmune diseases are available and are useful for assessing the efficacy of the combinations of the invention in these diseases. Other autoimmune diseases include, without limitation, alopecia areata, acquired hemophilia, ankylosing spondylitis, antiphospholipid syndrome, autoimmune hepatitis, autoimmune hemolytic anemia, Behçet's syndrome, cardiomyopathy, celiac sprue dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, discoid lupus, essential mixed cryoglobulinemia, fibromyalgia, fibromyositis, Guillain-Barré syndrome, idiopathic pulmonary fibrosis, idiopathic thrombocytopenic purpura, IgA nephropathy, juvenile arthritis, lichen planus, myasthenia gravis, polyarteritis nodosa, polychondritis, polyglandular syndromes, dermatomyositis, primary agammaglobulinemia, primary biliary cirrhosis, psoriasis, Raynaud's phenomena, Reiter's syndrome, sarcoidosis, stiffman syndrome, Takayasu arthritis, temporal arteritis/giant cell arteritis, uveitis, vasculitis, and vitiligo.

In several autoimmune diseases antibodies to self antigens are frequently observed. For example for systemic lupus erythematosus autoantibodies have been described to single-stranded and double-stranded DNA or RNA. Vallin, H. et al., (1999) *J Immunol* 163:6306-13; Hoet, R. M. et al., (1999) *J Immunol* 163:3304-12; ven Venrooij (1990) *J Clin Invest* 86:2154-60. The levels of autoantibodies found in the serum of autoimmune patients very often are found to correlate with disease severity. The pattern of autoantibodies that arise, e.g., in human SLE, suggest that intact macromolecular particles, such as RNA- or DNA-containing complexes, could themselves be immunogenic and anti-nucleic acid antibodies could therefore arise. Lotz, M. et al., (1992) *Mol Biol Rep* 16:127; Mohan C et al., (1993) *J Exp Med* 177:1367-81. Such DNA or RNA released from, e.g., apoptotic cells or DNA- or RNA-containing microbes present in serum of autoimmune patients, could be responsible for inflammation that contributes to the autoimmune disease. Fatenejad, S. (1994) *J Immunol* 152:5523-31; Malmegrim, K. C. et al., (2002) *Isr Med Assoc J* 4:706-12; Newkirk, M. M. et al., (2001) *Arthritis Res* 3:253-8. Indeed CpG-containing sequences could be identified from SLE serum that induces an efficient immune response dominated by IFN-α secretion that is thought to contribute the development of to autoimmune diseases. Magnusson, M. et al., (2001) *Scand J Immunol* 54:543-50; Rönblom, L. et al., (2001) *J Exp Med* 194:F59-63. In addition, the epitopes for anti-RNA antibodies could be identified and are composed of G,U-rich sequences. Tsai, D. E. et al., (1992) *Proc Natl Aced Sci USA* 89:8864-8; Tsai, D. E. et al., (1993) *J Immunol* 150:1137-45. G,U-rich sequences appear to be natural ligands for TLR7 and TLR8 and, therefore, can mediate immune stimulatory responses that in principle could contribute to autoimmune diseases or the development of autoimmune diseases. PCT/US03/10406. Given the importance of immune stimulation mediated by serum CpG DNA or G,U-rich RNA that are targets for autoantibodies, the present invention is provides a method for treating a condition associated with CpG DNA- or RNA-mediated immunostimulation in a subject having or being at risk of having an autoimmune disease.

A subject shall mean a human or vertebrate animal including but not limited to a dog, cat, horse, cow, pig, sheep, goat, turkey, chicken, primate, e.g., monkey, and fish (aquaculture species), e.g., salmon. Preferably the subject is a mammal and more preferably a human. Thus, the invention can also be used to treat cancer and tumors, infections, and allergy/asthma in non human subjects. Cancer is one of the leading causes of death in companion animals (i.e., cats and dogs).

As used herein, the term treat, treated, or treating when used with respect to an disorder such as an infectious disease, cancer, allergy, or asthma refers to a prophylactic treatment which increases the resistance of a subject to development of the disease (e.g., to infection with a pathogen) or, in other words, decreases the likelihood that the subject will develop the disease (e.g., become infected with the pathogen) as well as a treatment after the subject has developed the disease in order to fight the disease (e.g., reduce or eliminate the infection) or prevent the disease from becoming worse.

The Py-Pu immunostimulatory oligonucleotides may be administered as part of a therapeutic protocol, either alone or in conjunction with other therapies or medicaments. As used herein, a "therapeutic protocol" refers to procedures that include but are not limited to surgery, radiation, administration of a therapeutic medicament. A therapeutic medicament administered as part of a therapeutic protocol may be formulated or associated with a targeting molecule. A "targeting molecule" as used herein refers to any molecule such as an antigen that will target the immunostimulatory oligonucleotide to a particular site on or in a cell. In one embodiment the immunostimulatory oligonucleotide is conjugated to the targeting molecule. In another embodiment the targeting molecule is administered in conjunction with the immunostimulatory oligonucleotide without conjugation. In some instances the targeting molecule and the immunostimulatory oligonucleotide may be enclosed in a delivery vehicle such as a liposome. In other instances the targeting molecule is attached to the outside of the delivery vehicle.

In the instances when the Py-Pu oligonucleotide is administered with an antigen, the subject may be exposed to the antigen. As used herein, the term exposed to refers to either the active step of contacting the subject with an antigen or the passive exposure of the subject to the antigen in vivo. Methods for the active exposure of a subject to an antigen are well-known in the art. In general, an antigen is administered directly to the subject by any means such as intravenous, intramuscular, oral, transdermal, mucosal, intranasal, intratracheal, or subcutaneous administration. The antigen can be administered systemically or locally. Methods for administering the antigen and the Py-Pu immunostimulatory oligonucleotide are described in more detail below. A subject is passively exposed to an antigen if an antigen becomes available for exposure to the immune cells in the body. A subject may be passively exposed to an antigen, for instance, by entry of a foreign pathogen into the body or by the development of a tumor cell expressing a foreign antigen on its surface.

The methods in which a subject is passively exposed to an antigen can be particularly dependent on timing of administration of the Py-Pu immunostimulatory oligonucleotide. For instance, in a subject at risk of developing a cancer or an infectious disease or an allergic or asthmatic response, the subject may be administered the Py-Pu immunostimulatory oligonucleotide on a regular basis when that risk is greatest, i.e., during allergy season or after exposure to a cancer causing agent. Additionally the Py-Pu immunostimulatory oligonucleotide may be administered to travelers before they travel to foreign lands where they are at risk of exposure to infectious agents. Likewise the Py-Pu immunostimulatory oligonucleotide may be administered to soldiers or civilians at risk of exposure to biowarfare to induce a systemic or mucosal immune response to the antigen when and if the subject is exposed to it.

An antigen is a molecule capable of provoking an immune response. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and muticellular organisms such as parasites and allergens. The term antigen broadly includes any type of molecule which is recognized by a host immune system as being foreign. Antigens include but are not limited to cancer antigens, microbial antigens, and allergens.

A cancer antigen as used herein is a compound, such as a peptide or protein, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, *Cancer Research,* 54:1055, by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

A microbial antigen as used herein is an antigen of a microorganism and includes but is not limited to virus, bacteria, parasites, and fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

Viruses are small infectious agents which generally contain a nucleic acid core and a protein coat, but are not independently living organisms. Viruses can also take the form of infectious nucleic acids lacking a protein. A virus cannot survive in the absence of a living cell within which it can replicate. Viruses enter specific living cells either by endocytosis or direct injection of DNA (phage) and multiply, causing disease. The multiplied virus can then be released and infect additional cells. Some viruses are DNA-containing viruses and others are RNA-containing viruses. DNA viruses include Pox, Herpes, Adeno, Papova, Parvo, and Hepadna. RNA viruses include Picorna, Calici, Astro, Toga, Flavi, Corona, Paramyxo, Orthomyxo, Bunya, Arena, Rhabdo, Filo, Boma, Reo, and Retro. In some aspects, the invention also intends to treat diseases in which prions are implicated in disease progression such as for example bovine spongiform encephalopathy (i.e., mad cow disease, BSE) or scrapie infection in animals, or Creutzfeldt-Jakob disease in humans.

Viruses include, but are not limited to, enteroviruses (including, but not limited to, viruses that the family picornaviridae, such as polio virus, Coxsackie virus, echo virus), rotaviruses, adenovirus, and hepatitis virus, such as hepatitis A, B, C D and E. Specific examples of viruses that have been found in humans include but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papillomaviruses, polyoma viruses); Adenoviridae (most adenoviruses); Herpesviridae (herpes simplex virus (HSV) 1 and 2, varicella zoster virus, cytomegalovirus (CMV)); Poxviridae (variola viruses, vaccinia viruses, pox viruses); Iridoviridae (e.g., African swine fever virus); and other viruses acute laryngotracheobronchitis virus, Alphavirus, Kaposi's sarcoma-associated herpesvirus, Newcastle disease virus, Nipah virus, Norwalk virus, Papillomavirus, parainfluenza virus, avian influenza, SARs virus, West Nile virus.

Both gram negative and gram positive bacteria are infectious agents in vertebrate animals. Such gram positive bacteria include, but are not limited to, *Pasteurella* species, Staphylococci species, and *Streptococcus* species. Gram negative bacteria include, but are not limited to, *Escherichia coli, Pseudomonas* species, and *Salmonella* species. Specific examples of infectious bacteria include but are not limited to, *Helicobacter pyloris, Borelia burgdorferi, Legionella pneumophilia, Mycobacteria* sps (e.g., *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia*, and *Actinomyces israelli*.

Examples of fungi include *Cryptococcus neoformans, Histoplasma capsulatum, Coccidioides immitis, Blastomyces dermatitidis, Chlamydia trachomatis, Candida albicans*.

Other infectious organisms (i.e., protists) include *Plasmodium* spp. such as *Plasmodium falciparum, Plasmodium malariae, Plasmodium ovale*, and *Plasmodium vivax* and *Toxoplasma gondii*. Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

Other medically relevant microorganisms have been described extensively in the literature, e.g., see C. G. A. Thomas, *Medical Microbiology*, Bailliere Tindall, Great Britain 1983, the entire contents of which is hereby incorporated by reference.

An allergen refers to a substance (antigen) that can induce an allergic or asthmatic response in a susceptible subject. The list of allergens is enormous and can include pollens, insect venoms, animal dander dust, fungal spores and drugs (e.g., penicillin). Examples of natural, animal and plant allergens include but are not limited to proteins specific to the following genuses: *Canine (Canis familiaris); Dermatophagoides* (e.g., *Dermatophagoides farinae); Felis (Felis domesticus); Ambrosia (Ambrosia artemiisfolia; Lolium* (e.g., *Lolium perenne* or *Lolium multiflorum); Cryptomeria (Cryptomeria japonica); Alternaria (Alternaria alternata); Alder, Alnus (Alnus gultinoasa); Betula (Betula verrucosa); Quercus (Quercus alba); Olea (Olea europa); Artemisia (Artemisia vulgaris); Plantago* (e.g., *Plantago lanceolata); Parietaria* (e.g., *Parietaria officinalis* or *Parietaria judaica); Blattella* (e.g., *Blattella germanica); Apis* (e.g., *Apis multiflorum); Cupressus* (e.g., *Cupressus sempervirens, Cupressus arizonica* and *Cupressus macrocarpa); Juniperus* (e.g., *Juniperus sabinoides, Juniperus virginiana, Juniperus communis* and *Juniperus ashei); Thuya* (e.g., *Thuya orientalis); Chamaecyparis* (e.g., *Chamaecyparis obtusa); Periplaneta* (e.g., *Periplaneta americana); Agropyron* (e.g., *Agropyron repens); Secale* (e.g., *Secale cereale); Triticum* (e.g., *Triticum aestivum); Dactylis* (e.g., *Dactylis glomerata); Festuca* (e.g., *Festuca elatior); Poa* (e.g., *Poa pratensis* or *Poa compressa); Avena* (e.g., *Avena sativa); Holcus* (e.g., *Holcus lanatus); Anthoxanthum* (e.g., *Anthoxanthum odoratum); Arrhenatherum* (e.g., *Arrhenatherum elatius); Agrostis* (e.g., *Agrostis alba); Phleum* (e.g., *Phleum pratense); Phalaris* (e.g., *Phalaris arundinacea); Paspalum* (e.g., *Paspalum notatum); Sorghum* (e.g., *Sorghum halepensis);* and *Bromus* (e.g., *Bromus inermis*).

The Py-Pu immunostimulatory oligonucleotides of the instant invention can be administered alone or combined with other therapeutic agents such as adjuvants to enhance immune responses. The immunostimulatory oligonucleotide and other therapeutic agent may be administered simultaneously or sequentially or as part of a therapeutic protocol. When the other therapeutic agents are administered simultaneously they can be administered in the same or separate formulations, but are administered at the same time. The other therapeutic agents are administered sequentially with one another and with immunostimulatory oligonucleotide, when the administration of the other therapeutic agents and the immunostimulatory oligonucleotide is temporally separated. The separation in time between the administrations of these compounds may be a matter of minutes or it may be longer. Other therapeutic agents include but are not limited to adjuvants, cytokines, antibodies, antigens, medicaments, etc. In some instances it may be advantageous for the Py-Pu immunostimulatory oligonucleotides to be linked to a therapeutic agent or medicament. This linkage may be covalent or non-covalent. A covalent linkage is one in which the agent and the oligonucleotide are attached through a covalent bond. The covalent linkage between the oligonucleotide and the antigen can be any suitable type of covalent linkage, provided the immunostimulatory oligonucleotide and the antigen when so joined retain measurable functional activity of each individual component. The covalent linkage may be direct or indirect, e.g., through a linker moiety. The covalently linked immunostimulatory oligonucleotide and antigen may be processed within a cell to release one from the other. In this way delivery to a cell of either component may be enhanced compared to its delivery if administered as a separate preparation or separate component.

A non-covalent linkage is one in which there is no covalent bond, such as association through hydrogen bonding or inside a delivery vehicle such as a microparticle.

The oligonucleotides of the invention may be administered to a subject with an anti-microbial agent. An anti-microbial agent, as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent," "anti-bacterial agent," "anti-viral agent," "anti-fungal agent," "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells. Anti-viral agents can be isolated from natural sources or synthesized and are useful for killing or inhibiting viruses. Anti-fungal agents are used to treat superficial fungal infections as well as opportunistic and primary systemic fungal infections. Anti-parasite agents kill or inhibit parasites.

Examples of anti-parasitic agents, also referred to as parasiticides useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide some of which are used alone or in combination with others.

Antibacterial agents kill or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g., amantadine), synthesis or translation of viral mRNA (e.g., interferon), replication of viral RNA or DNA (e.g., nucleotide analogues), maturation of new virus proteins (e.g., protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, and resimiquimod.

The interferons are cytokines which are secreted by virus-infected cells as well as immune cells. The interferons function by binding to specific receptors on cells adjacent to the infected cells, causing the change in the cell which protects it from infection by the virus. α and β-interferon also induce the expression of Class I and Class II MHC molecules on the surface of infected cells, resulting in increased antigen presentation for host immune cell recognition. α and β-interferons are available as recombinant forms and have been used for the treatment of chronic hepatitis B and C infection. At the dosages which are effective for anti-viral therapy, interferons have severe side effects such as fever, malaise and weight loss.

Anti-viral agents useful in the invention include but are not limited to immunoglobulins, amantadine, interferons, nucleotide analogues, and protease inhibitors. Specific examples of anti-virals include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscamet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, imidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g., chitinase) or immunosuppression (501 cream).

The Py-Pu immunostimulatory oligonucleotides may be administered with an asthma medicament. Asthma medicaments include, but are not limited, PDE-4 inhibitors, bronchodilator/beta-2 agonists, K+ channel openers, VLA-4 antagonists, neurokin antagonists, thromboxane A2 (TXA2) synthesis inhibitors, xanthines, arachidonic acid antagonists, 5 lipoxygenase inhibitors, TXA2 receptor antagonists, TXA2 antagonists, inhibitor of 5-lipox activation proteins, and protease inhibitors.

Bronchodilator/$\beta_2$ agonists are a class of compounds which cause bronchodilation or smooth muscle relaxation.

Bronchodilator/β₂ agonists include, but are not limited to, salmeterol, salbutamol, albuterol, terbutaline, D2522/formoterol, fenoterol, bitolterol, pirbuerol methylxanthines and orciprenaline. Long-acting β₂ agonists and bronchodilators are compounds which are used for long-term prevention of symptoms in addition to the anti-inflammatory therapies. Long-acting β₂ agonists include, but are not limited to, salmeterol and albuterol. These compounds are usually used in combination with corticosteroids and generally are not used without any inflammatory therapy. They have been associated with side effects such as tachycardia, skeletal muscle tremor, hypokalemia, and prolongation of QTc interval in overdose.

Methylxanthines, including for instance theophylline, have been used for long-term control and prevention of symptoms. These compounds cause bronchodilation resulting from phosphodiesterase inhibition and likely adenosine antagonism. Dose-related acute toxicities are a particular problem with these types of compounds. As a result, routine serum concentration must be monitored in order to account for the toxicity and narrow therapeutic range arising from individual differences in metabolic clearance. Side effects include tachycardia, tachyarrhythmias, nausea and vomiting, central nervous system stimulation, headache, seizures, hematemesis, hyperglycemia and hypokalemia. Short-acting β₂ agonists include, but are not limited to, albuterol, bitolterol, pirbuterol, and terbutaline. Some of the adverse effects associated with the administration of short-acting β₂ agonists include tachycardia, skeletal muscle tremor, hypokalemia, increased lactic acid, headache, and hyperglycemia.

Chromolyn sodium and nedocromil are used as long-term control medications for preventing primarily asthma symptoms arising from exercise or allergic symptoms arising from allergens. These compounds are believed to block early and late reactions to allergens by interfering with chloride channel function. They also stabilize mast cell membranes and inhibit activation and release of mediators from inosineophils and epithelial cells. A four to six week period of administration is generally required to achieve a maximum benefit.

Anticholinergics are generally used for the relief of acute bronchospasm. These compounds are believed to function by competitive inhibition of muscarinic cholinergic receptors. Anticholinergics include, but are not limited to, ipratropium bromide. These compounds reverse only cholinerigically-mediated bronchospasm and do not modify any reaction to antigen. Side effects include drying of the mouth and respiratory secretions, increased wheezing in some individuals, and blurred vision if sprayed in the eyes.

The immunostimulatory oligonucleotides of the invention may also be administered in conjunction with an anti-allergy therapy. Conventional methods for treating or preventing allergy have involved the use of allergy medicaments or desensitization therapies. Some evolving therapies for treating or preventing allergy include the use of neutralizing anti-IgE antibodies. Anti-histamines and other drugs which block the effects of chemical mediators of the allergic reaction help to regulate the severity of the allergic symptoms but do not prevent the allergic reaction and have no effect on subsequent allergic responses. Desensitization therapies are performed by giving small doses of an allergen, usually by injection under the skin, in order to induce an IgG-type response against the allergen. The presence of IgG antibody helps to neutralize the production of mediators resulting from the induction of IgE antibodies, it is believed. Initially, the subject is treated with a very low dose of the allergen to avoid inducing a severe reaction and the dose is slowly increased. This type of therapy is dangerous because the subject is actually administered the compounds which cause the allergic response and severe allergic reactions can result.

Allergy medicaments include, but are not limited to, anti-histamines, corticosteroids, and prostaglandin inducers. Anti-histamines are compounds which counteract histamine released by mast cells or basophils. These compounds are well known in the art and commonly used for the treatment of allergy. Anti-histamines include, but are not limited to, acrivastine, astemizole, azatadine, azelastine, betatastine, brompheniramine, buclizine, cetirizine, cetirizine analogues, chlorpheniramine, clemastine, CS 560, cyproheptadine, desloratadine, dexchlorpheniramine, ebastine, epinastine, fexofenadine, HSR 609, hydroxyzine, levocabastine, loratidine, methscopolamine, mizolastine, norastemizole, phenindamine, promethazine, pyrilamine, terfenadine, and tranilast.

Corticosteroids include, but are not limited to, methylprednisolone, prednisolone, prednisone, beclomethasone, budesonide, dexamethasone, flunisolide, fluticasone propionate, and triamcinolone. Although dexamethasone is a corticosteroid having anti-inflammatory action, it is not regularly used for the treatment of allergy or asthma in an inhaled form because it is highly absorbed and it has long-term suppressive side effects at an effective dose. Dexamethasone, however, can be used according to the invention for treating allergy or asthma because when administered in combination with a composition of the invention it can be administered at a low dose to reduce the side effects. Some of the side effects associated with corticosteroid use include cough, dysphonia, oral thrush (candidiasis), and in higher doses, systemic effects, such as adrenal suppression, glucose intolerance, osteoporosis, aseptic necrosis of bone, cataract formation, growth suppression, hypertension, muscle weakness, skin thinning, and easy bruising. Barnes & Peterson (1993) *Am Rev Respir Dis* 148:S1-S26; and Kamada A K et al., (1996) *Am J Respir Crit. Care Med* 153:1739-48.

The immunostimulatory composition of the invention may also be administered in conjunction with an anti-cancer therapy. Anti-cancer therapies include cancer medicaments, radiation, and surgical procedures. As used herein, a "cancer medicament" refers to an agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

Additionally, the methods of the invention are intended to embrace the use of more than one cancer medicament along with the Py-Pu immunostimulatory oligonucleotides. As an example, where appropriate, the Py-Pu immunostimulatory oligonucleotides may be administered with both a chemotherapeutic agent and an immunotherapeutic agent. Alternatively, the cancer medicament may embrace an immunotherapeutic agent and a cancer vaccine, or a chemotherapeutic agent and a cancer vaccine, or a chemotherapeutic agent, an immunotherapeutic agent and a cancer vaccine all administered to one subject for the purpose of treating a subject having a cancer or at risk of developing a cancer.

The chemotherapeutic agent may be selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2' deoxycoformycin), Semustine (methyl-CCNU), Teniposide (VM-26) and Vindesine sulfate, but it is not so limited.

The immunotherapeutic agent may be selected from the group consisting of 3622W94, 4B5, ANA Ab, anti-FLK-2, anti-VEGF, ATRAGEN, AVASTIN (bevacizumab; Genentech), BABS, BEC2, BEXXAR (tositumomab; GlaxoSmithKline), C225, CAMPATH (alemtuzumab; Genzyme Corp.), CEACIDE, CMA 676, EMD-72000, ERBITUX (cetuximab; ImClone Systems, Inc.), Gliomab-H, GNI-250, HERCEPTIN (trastuzumab; Genentech), IDEC-Y2B8, ImmuRAIT-CEA, ior c5, ior egf.r3, ior t6, LDP-03, LymphoCide, MDX-11, MDX-22, MDX-210, MDX-220, MDX-260, MDX-447, MELIMMUNE-1, MELIMMUNE-2, Monopharm-C, NovoMAb-G2, Oncolym, OV103, Ovarex, Panorex, Pretarget, Quadramet, Ributaxin, RITUXAN (rituximab; Genentech), SMART 1D10 Ab, SMART ABL 364 Ab, SMART M195, TNT, and ZENAPAX (daclizumab; Roche), but it is not so limited.

The cancer vaccine may be selected from the group consisting of EGF, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vaccine, TA-HPV, TA-CIN, DISC-virus and ImmuCyst/TheraCys, but it is not so limited.

The use of Py-Pu immunostimulatory oligonucleotides in conjunction with immunotherapeutic agents such as monoclonal antibodies is able to increase long-term survival through a number of mechanisms including significant enhancement of ADCC (as discussed above), activation of natural killer (NK) cells and an increase in IFNα levels. The nucleic acids when used in combination with monoclonal antibodies serve to reduce the dose of the antibody required to achieve a biological result.

As used herein, the terms cancer antigen and tumor antigen are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

The compositions of the invention may also be administered with non-nucleic acid adjuvants. A non-nucleic acid adjuvant is any molecule or compound except for the Py-Pu immunostimulatory oligonucleotides described herein which can stimulate the humoral and/or cellular immune response. Non-nucleic acid adjuvants include, for instance, adjuvants that create a depo effect, immune stimulating adjuvants, and adjuvants that create a depo effect and stimulate the immune system.

The Py-Pu immunostimulatory oligonucleotides are also useful as mucosal adjuvants. It has previously been discovered that both systemic and mucosal immunity are induced by mucosal delivery of Py-Pu nucleic acids. Thus, the oligonucleotides may be administered in combination with other mucosal adjuvants.

Immune responses can also be induced or augmented by the co-administration or co-linear expression of cytokines (Bueler & Mulligan, 1996; Chow et al., 1997; Geissler et al., 1997; Iwasaki et al., 1997; Kim et al., 1997) or B-7 co-stimulatory molecules (Iwasaki et al., 1997; Tsuji et al., 1997) with the Py-Pu immunostimulatory oligonucleotides. The term cytokine is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to IL-1, IL-2, IL-4, IL-5, IL-6, IL-7, IL-10, IL-12, IL-15, IL-18, granulocyte-macrophage colony stimulating factor (GM-CSF), granulocyte colony stimulating factor (G-CSF), interferon-γ (γ-IFN), IFN-α, tumor necrosis factor (TNF), TGF-β, FLT-3 ligand, and CD40 ligand. Cytokines play a role in directing the T cell response. Helper (CD4+) T cells orchestrate the immune response of mammals through production of soluble factors that act on other immune system cells, including other T cells. Most mature CD4+ T helper cells express one of two cytokine profiles: Th1 or Th2. In some embodiments it is preferred that the cytokine be a Th1 cytokine.

The oligonucleotides are also useful for redirecting an immune response from a Th2 immune response to a Th1 immune response. This results in the production of a relatively balanced Th1/Th2 environment. Redirection of an immune response from a Th2 to a Th1 immune response can be assessed by measuring the levels of cytokines produced in response to the nucleic acid (e.g., by inducing monocytic cells and other cells to produce Th1 cytokines, including IL-12, IFN-α and GM-CSF). The redirection or rebalance of the immune response from a Th2 to a Th1 response is particularly useful for the treatment or prevention of asthma. For instance, an effective amount for treating asthma can be that amount; useful for redirecting a Th2 type of immune response that is associated with asthma to a Th1 type of response or a balanced Th1/Th2 environment. Th2 cytokines, especially IL-4 and IL-5 are elevated in the airways of asthmatic subjects. The Py-Pu immunostimulatory oligonucleotides of the invention cause an increase in Th1 cytokines which helps to rebalance the immune system, preventing or reducing the adverse effects associated with a predominately Th2 immune response.

The oligonucleotides of the invention may also be useful for treating airway remodeling. Airway remodeling results from smooth muscle cell proliferation and/or submucosal thickening in the airways, and ultimately causes narrowing of the airways leading to restricted airflow. The oligonucleotides of the invention may prevent further remodeling and possibly even reduce tissue buildup resulting from the remodeling process.

The oligonucleotides are also useful for improving survival, differentiation, activation and maturation of dendritic cells. The Py-Pu immunostimulatory oligonucleotides have the unique capability to promote cell survival, differentiation, activation and maturation of dendritic cells.

The Py-Pu immunostimulatory oligonucleotides may be directly administered to the subject or may be administered in conjunction with a nucleic acid delivery complex. A nucleic acid delivery complex shall mean a nucleic acid molecule associated with (e.g., ionically or covalently bound to; or encapsulated within) a targeting means (e.g., a molecule that results in higher affinity binding to target cell. Examples of nucleic acid delivery complexes include nucleic acids associated with a sterol (e.g., cholesterol), a lipid (e.g., a cationic lipid, virosome or liposome), or a target cell specific binding agent (e.g., a ligand recognized by target cell specific receptor). Preferred complexes may be sufficiently stable in vivo to prevent significant uncoupling prior to internalization by the target cell. However, the complex can be cleavable under appropriate conditions within the cell so that the oligonucleotide is released in a functional form.

Delivery vehicles or delivery devices for delivering antigen and oligonucleotides to surfaces have been described. The Py-Pu immunostimulatory oligonucleotide and/or the antigen and/or other therapeutics may be administered alone (e.g., in saline or buffer) or using any delivery vehicles known in the art. In one aspect the invention provides a pharmaceutical composition including the composition of any of the foregoing aspects of the invention, in association with a delivery vehicle chosen from a cationic lipid, a liposome, a live bacterial vector (e.g., *Salmonella, Escherichia coli, Bacillus calmatte-guerin, Shigella, Lactobacillus*), a live viral vector (e.g., Vaccinia, adenovirus, Herpes Simplex), a cochleate, a virosome, an immune-stimulating complex (ISCOM), a microparticle, a microsphere, a nanosphere, a unilamellar vesicle (LUV), a multilamellar vesicle, an oil-in-water emulsion, a water-in-oil emulsion, an emulsome, a polycationic peptide, a microsphere, a nucleic acid vaccine, a polymer, a polymer ring, a proteosome, sodium fluoride, or a transgenic plant and, optionally, a pharmaceutically acceptable carrier. In one embodiment according to this aspect of the invention the pharmaceutical composition includes an antigen. In another embodiment according to this aspect of the invention the pharmaceutical composition includes an anti-infective, cancer, asthma, allergy, or inflammation or other medicament.

In one embodiment the immunostimulatory oligonucleotide is administered with a cationic lipid and the cationic lipid is DOTAP (N-[1-(2,3-dioleoyloxy)propy-I]-N,N,N-trimethylammonium methyl-sulfate). Other agents with similar properties including trafficking to the endosomal compartment can be used in place of or in addition to to DOTAP. Other lipid formulations include, for example, as EFFECTENE™ (a non-liposomal lipid with a special DNA condensing enhancer) and SUPERFECT™ (a novel acting dendrimeric technology). Liposomes are commercially available from Gibco BRL, for example, as LIPOFECTIN™ and LIPOFECTACE™, which are formed of cationic lipids such as N-[1-(2,3 dioleyloxy)-propyl]-N,N, N-trimethylammonium chloride (DOTMA) and dimethyl dioctadecylammonium bromide (DDAB). Methods for making liposomes are well known in the art and have been described in many publications. Liposomes also have been reviewed by Gregoriadis G (1985) *Trends Biotechnol* 3:235-241.

Liposomes may be targeted to a particular tissue by coupling the liposome to a specific ligand such as a monoclonal antibody, sugar, glycolipid, or protein. Ligands which may be useful for targeting a liposome to an immune cell include, but are not limited to: intact or fragments of molecules which interact with immune cell specific receptors and molecules, such as antibodies, which interact with the cell surface markers of immune cells. Such ligands may easily be identified by binding assays well known to those of skill in the art. In still other embodiments, the liposome may be targeted to the cancer by coupling it to a one of the immunotherapeutic antibodies discussed earlier. Additionally, the vector may be coupled to a nuclear targeting peptide, which will direct the vector to the nucleus of the host cell.

In one embodiment, the vehicle is a biocompatible microparticle or implant that is suitable for implantation or administration to the mammalian recipient. Exemplary bio-erodible implants that are useful in accordance with this method are described in published International Application WO 95/24929, entitled "Polymeric Gene Delivery System." WO 95/24929 describes a biocompatible, preferably biodegradable polymeric matrix for containing an exogenous gene under the control of an appropriate promoter. The polymeric matrix can be used to achieve sustained release of the therapeutic agent in the subject.

The polymeric matrix preferably is in the form of a microparticle such as a microsphere (wherein the nucleic acid and/or the other therapeutic agent is dispersed throughout a solid polymeric matrix) or a microcapsule (wherein the nucleic acid and/or the other therapeutic agent is stored in the core of a polymeric shell). Other forms of the polymeric matrix for containing the therapeutic agent include films, coatings, gels, implants, and stents. The size and composition of the polymeric matrix device is selected to result in favorable release kinetics in the tissue into which the matrix is to introduced. The size of the polymeric matrix further is selected according to the method of delivery which is to be used, typically injection into a tissue or administration of a suspension by aerosol into the nasal and/or pulmonary areas. Preferably when an aerosol route is used the polymeric matrix and the nucleic acid and/or the other therapeutic agent are encompassed in a surfactant vehicle. The polymeric matrix composition can be selected to have both favorable degradation rates and also to be formed of a material which is bioadhesive, to further increase the effectiveness of transfer when the matrix is administered to a nasal and/or pulmonary surface that has sustained an injury. The matrix composition also can be selected not to degrade, but rather, to release by diffusion over an extended period of time. In some preferred embodiments, the nucleic acid are administered to the subject via an implant while the other therapeutic agent is administered acutely. Biocompatible microspheres that are suitable for delivery, such as oral or mucosal delivery, are disclosed in Chickering et al., (1996) *Biotech Bioeng* 52:96-101 and Mathiowitz, E. et al., (1997) *Nature* 386:410-414 and PCT Pat. Application WO97/03702.

Both non-biodegradable and biodegradable polymeric matrices can be used to deliver the nucleic acid and/or the other therapeutic agent to the subject. Biodegradable matrices are preferred. Such polymers may be natural or synthetic polymers. The polymer is selected based on the period of time over which release is desired, generally in the order of a few hours to a year or longer. Typically, release over a period ranging from between a few hours and three to twelve months is most desirable, particularly for the nucleic acid agents. The polymer optionally is in the form of a hydrogel that can absorb up to about 90% of its weight in water and further, optionally is cross-linked with multi-valent ions or other polymers.

Bioadhesive polymers of particular interest include bioerodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The term effective amount of a Py-Pu immunostimulatory oligonucleotide refers to the amount necessary or sufficient to realize a desired biologic effect. For example, an effective amount of a Py-Pu immunostimulatory oligonucleotide administered with an antigen for inducing mucosal immunity is that amount necessary to cause the development of IgA in response to an antigen upon exposure to the antigen, whereas that amount required for inducing systemic immunity is that amount necessary to cause the development of IgG in response to an antigen upon exposure to the antigen. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular Py-Pu immunostimulatory oligonucleotide being administered the size of the subject, or the severity of the disease or condition. One of ordinary skill in the art can empirically determine the effective amount of a particular Py-Pu immunostimulatory oligonucleotide and/or antigen and/or other therapeutic agent without necessitating undue experimentation.

Subject doses of the compounds described herein for mucosal or local delivery typically range from about 0.1 µg to 10 mg per administration, which depending on the application could be given daily, weekly, or monthly and any other amount of time therebetween. More typically mucosal or local doses range from about 10 µg to 5 mg per administration, and most typically from about 100 µg to 1 mg, with 2-4 administrations being spaced days or weeks apart. More typically, immune stimulant doses range from 1 µg to 10 mg per administration, and most typically 10 µg to 1 mg, with daily or weekly administrations. Subject doses of the compounds described herein for parenteral delivery for the purpose of inducing an antigen-specific immune response, wherein the compounds are delivered with an antigen but not another therapeutic agent are typically 5 to 10,000 times higher than the effective mucosal dose for vaccine adjuvant or immune stimulant applications, and more typically 10 to 1,000 times higher, and most typically 20 to 100 times higher. Doses of the compounds described herein for parenteral delivery for the purpose of inducing an innate immune response or for increasing ADCC or for inducing an antigen specific immune response when the Py-Pu immunostimulatory oligonucleotides are administered in combination with other therapeutic agents or in specialized delivery vehicles typically range from about 0.1 µg to 10 mg per administration, which depending on the application could be given daily, weekly, or monthly and any other amount of time therebetween. More typically parenteral doses for these purposes range from about 10 µg to 5 mg per administration, and most typically from about 100 µg to 1 mg, with 2-4 administrations being spaced days or weeks apart. In some embodiments, however, parenteral doses for these purposes may be used in a range of 5 to 10,000 times higher than the typical doses described above.

For any compound described herein the therapeutically effective amount can be initially determined from animal models. A therapeutically effective dose can also be determined from human data for Py-Pu oligonucleotides which have been tested in humans (human clinical trials have been initiated) and for compounds which are known to exhibit similar pharmacological activities, such as other adjuvants, e.g., LT and other antigens for vaccination purposes. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The Py-Pu immunostimulatory oligonucleotides may be formulated. The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the Py-Pu immunostimulatory oligonucleotide can be administered to a subject by any mode that delivers the oligonucleotide to the desired surface, e.g., mucosal, systemic. Administering the pharmaceutical composition of the present invention may be accomplished by any means known to the skilled artisan. Routes of administration include but are not limited to oral, parenteral, intramuscular, intravenous, subcutaneous, mucosal, intranasal, sublingual, intratracheal, inhalation, ocular, vaginal, dermal, rectal, and by direct injection.

For oral administration, the compounds (i.e., Py-Pu immunostimulatory oligonucleotides, antigens and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e., EDTA for neutralizing internal acid conditions or may be administered without any carriers.

Also specifically contemplated are oral dosage forms of the above oligonucleotides. The oligonucleotides may be chemically modified so that oral delivery is efficacious. Generally, the chemical modification contemplated is the attachment of at least one moiety to the oligonucleotides itself, where said moiety permits (a) inhibition of proteolysis; and (b) uptake into the blood stream from the stomach or intestine. Also desired is the increase in overall stability of the oligonucleotides and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the oligonucleotides the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the oligonucleotide or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e., powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the oligonucleotide may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic. An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the oligonucleotide either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the oligonucleotides. The oligonucleotide is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13 (suppl. 5):143-146 (endothelin-1); Hubbard et al., 1989, Annals of Internal Medicine, Vol. III, pp. 206-212 (al-antitrypsin); Smith et al., 1989, J. Clin. Invest. 84:1145-1146 (a-1-proteinase); Oswein et al., 1990, "Aerosolization of Proteins," Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of oligonucleotide. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified oligonucleotide may also be prepared in different formulations depending on the type of chemical modification or the type of device employed.

Formulations suitable for use with a nebulizer, either jet or ultrasonic, will typically comprise oligonucleotide dissolved in water at a concentration of about 0.1 to 25 mg of biologically active oligonucleotide per mL of solution. The formulation may also include a buffer and a simple sugar (e.g., for oligonucleotide stabilization and regulation of osmotic pressure). The nebulizer formulation may also contain a surfactant, to reduce or prevent surface induced aggregation of the oligonucleotide caused by atomization of the solution in forming the aerosol.

Formulations for use with a metered-dose inhaler device will generally comprise a finely divided powder containing the oligonucleotide suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing oligonucleotide and may also include a bulking agent, such as lactose, sorbitol, sucrose, or mannitol in amounts which facilitate dispersal of the powder from the device, e.g., 50 to 90% by weight of the formulation. The oligonucleotide should most advantageously be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The Py-Pu immunostimulatory oligonucleotides and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a Py-Pu immunostimulatory oligonucleotide and optionally antigens and/or other therapeutic agents optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Materials and Methods

Oligodeoxynucleotides (ODN) and reagents

All ODN were synthesized following fast deprotection phosphoramidite chemistry protocols and controlled for identity and purity by Coley Pharmaceutical GmbH and had undetectable endotoxin levels (<0.1 EU/ml) measured by the Limulus assay (BioWhittaker, Verviers, Belgium). ODN were suspended in sterile, endotoxin-free Tris-EDTA (Sigma, Deisenhofen, Germany), and stored and handled under aseptic conditions to prevent both microbial and endotoxin contamination. All dilutions were carried out using endotoxin-free Tris-EDTA.

TLR9 Assays

HEK293 cells were transfected by electroporation with vectors expressing human TLR9 and a 6×NF-κB-luciferase reporter plasmid. Stable transfectants ($3 \times 10^4$ cells/well) were incubated indicated amounts of ODN for 16 h at 37° C. in a humidified incubator. Each data point was done in triplicate. Cells were lysed and assayed for luciferase gene activity (using the BriteLite kit from Perkin-Elmer, Zaventem, Belgium). Stimulation indices were calculated in reference to reporter gene activity of medium without addition of ODN.

Cell Purification

Peripheral blood buffy coat preparations from healthy human donors were obtained from the Blood Bank of the University of Düsseldorf (Germany) and PBMC were purified by centrifugation over Ficoll-Hypaque (Sigma). Cells were cultured in a humidified incubator at 37° C. in RPMI 1640 medium supplemented with 5% (v/v) heat inactivated human AB serum (BioWhittaker) or 10% (v/v) heat inactivated FCS, 2 mM L-glutamine, 100 U/ml penicillin and 100 µg/ml streptomycin (all from Sigma).

Cytokine Detection

PBMC were resuspended at a concentration of $5 \times 10^6$ cells/ml and added to 96 well round-bottomed plates (250 µl/well). PBMC were incubated with various ODN, ORN or nucleoside concentrations and culture supernatants (SN) were collected after the indicated time points. If not used immediately, SN were stored at −20° C. until required. For inhibitory experiments, cells were stimulated with the indicated TLR ligand concentration and nucleoside or ORN added. In some experiments, the second modified ORN was added 1 h after the start of the cell culture. Amounts of cytokines in the SN were assessed using an in-house ELISA for IFN-α developed using commercially available antibodies (PBL, New Brunswick, N.J., USA).

Example 1

Phosphonoacetate Backbone Modification at the CpG Motif Result in Increased TLR9 Activation It is known that oligonucleotides containing unmethylated CpG motifs are able to stimulate immune responses through the Toll-like receptor 9 (TLR9) pathway. Phosphorothioate (PS) oligonucleotides (ODN) show strong immune stimulatory activity which is only superseded by the semi-soft ODNs, in which the internucleotide linkage at CpG is a phosphodiester (PO) linkage. It has been generally assumed that the substituents at the phosphorus atom must have similar charge and size to obtain comparable activity. To investigate this relationship more fully, HEK 293 cells transfected with human TLR9 were incubated with ODNs comprising PO (SEQ ID NO: 7), PS (SEQ ID NO: 6), P-Me (SEQ ID NO:12) and phosphonoacetate (PA) (SEQ ID NO:8) backbone modifications at the CpG motif. SEQ ID NO:3 is a B class ODN with known activity. TLR9 activity was measured by luciferase assay using a 6×NF-κB-luciferase reporter plasmid. The comparison of PS with P-Me (methyl phosphonate) shows, however, that charge may not play a dominant role for activation of TLR9 activity (FIG. 1). In addition, enlarging the size of the substituent at the phosphorus from PO to PS significantly diminished activation of TLR9 activity. Therefore, it was very surprising that introduction of the PA linkage (larger than PO and P-Me) resulted in the best TLR9 activity observed by Applicants so far for a phosphate modification (FIG. 1). Table 1 shows a summary of the ODN sequences tested.

TABLE 1

| Seq ID No. | Sequence | Description |
|---|---|---|
| 3 | T*C-G*T*C-G*T*T*T*T*G*T*C-G*T*T*T*T*G*T*C-G*T*T | B class |
| 6 | T*G*T*C*G*T*T*T*T*T*T*T*T*T*T*T*T*T*T | B class PS |
| 7 | T*G*T*C-G*T*T*T*T*T*T*T*T*T*T*T*T*T*T | B class PO |
| 8 | T*G*T*C<G*T*T*T*T*T*T*T*T*T*T*T*T*T*T | B class PA |
| 12 | T*G*T*C§G*T*T*T*T*T*T*T*T*T*T*T*T*T*T | B class P-Me |

< phosphonoacetate internucleotide linkage
* phosphorothioate internucleotide linkage
- phosphodiester internucleotide linkage
§ methylphosphonate internucleotide linkage Example 2

Figure 2:
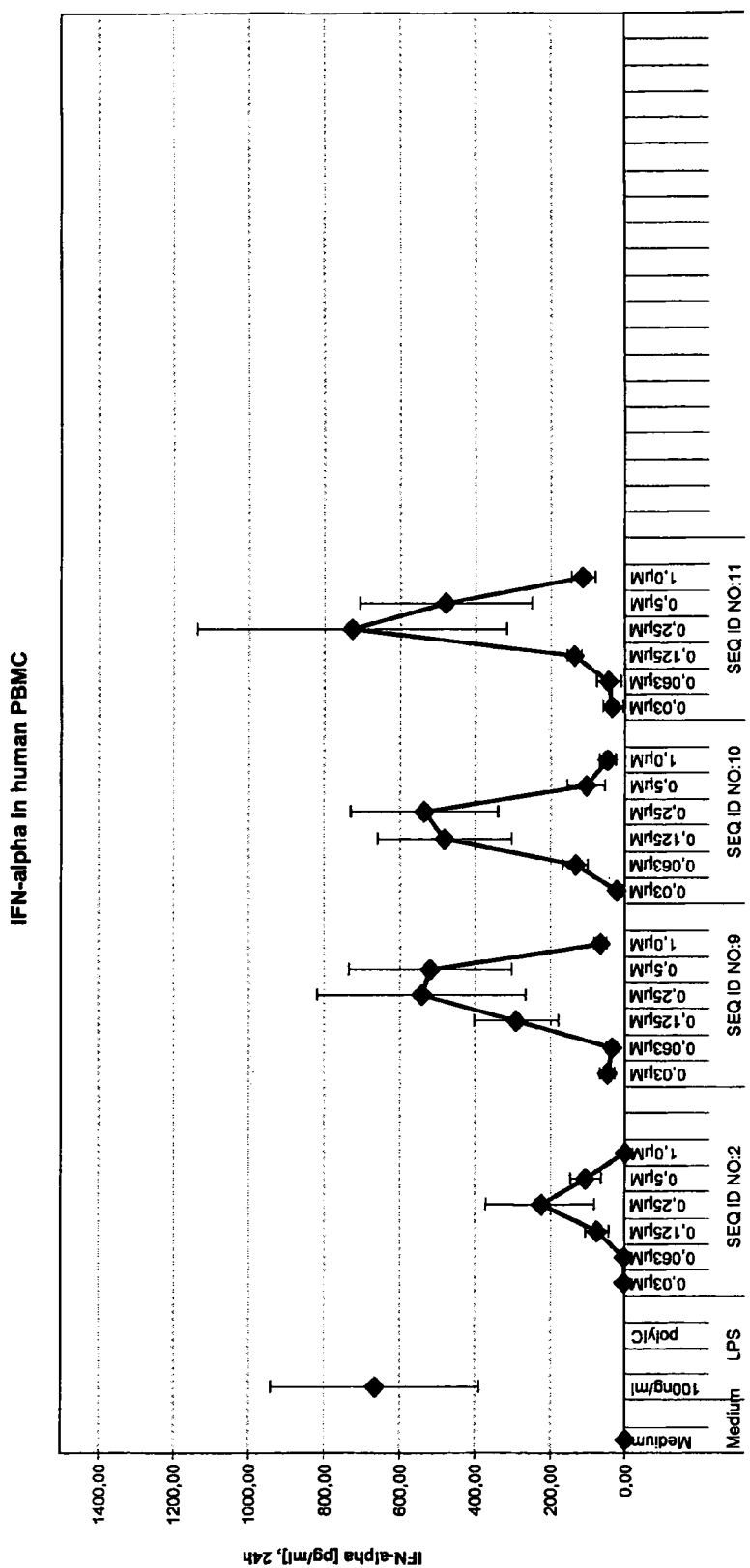
FIG. 2 is a graph showing interferon alpha (IFN-α) induction in human PBMCs following stimulation with PA ODN. The IFN-α production of semi-soft ODN with either one (SEQ ID NOs 9-10) or two (SEQ ID NO:11) PA modifications in a CpG motif was compared to a semi-soft ODN of the same sequence (SEQ ID NO:2), as measured by ELISA assay. The y-axis is IFN-α concentration in pg/ml and the x-axis is oligonucleotide concentration in pM.

Phosphonoacetate Backbone Modification at the CpG Motif Result in Increased IFN-α Production To investigate the effect of the PA modification in human cells, human PBMCs were isolated from whole blood and incubated with B class ODN with identical sequence but varying sites of PA modification. ODN were either unmodified (SEQ ID NO:33), modified at the first CpG motif (SEQ ID NO:8), modified at the second CpG motif (SEQ ID NO:9), or modified at both the first and second CpG motifs (SEQ ID NO:10). After incubation for 24 hours, IFN-α concentration was measured by ELISA assay. All three ODN with PA modifications induced more IFN-α than the unmodified ODN. SEQ ID NO:10 with two PA modifications appeared to induce slightly more IFN-α than the singly modified ODN (FIG. 2). Table 2 shows a summary of the ODN sequences tested.

TABLE 2

| Seq ID No. | Sequence | Description |
|---|---|---|
| 2 | T*C-G*T*C-G*T*T*T-G*C-G*T*C-G*T*T | B class |
| 9 | T*C<G*T*C-G*T*T*T-G*C-G*T*C-G*T*T | B class |
| 10 | T*C-G*T*C<G*T*T*T-G*C-G*T*C-G*T*T | B class |
| 11 | T*C<G*T*C<G*T*T*T-G*C-G*T*C-G*T*T | B class |

< phosphonoacetate internucleotide linkage
* phosphorothioate internucleotide linkage
- phosphodiester internucleotide linkage
§ methylphosphonate internucleotide linkage Example 3

Figure 3A:
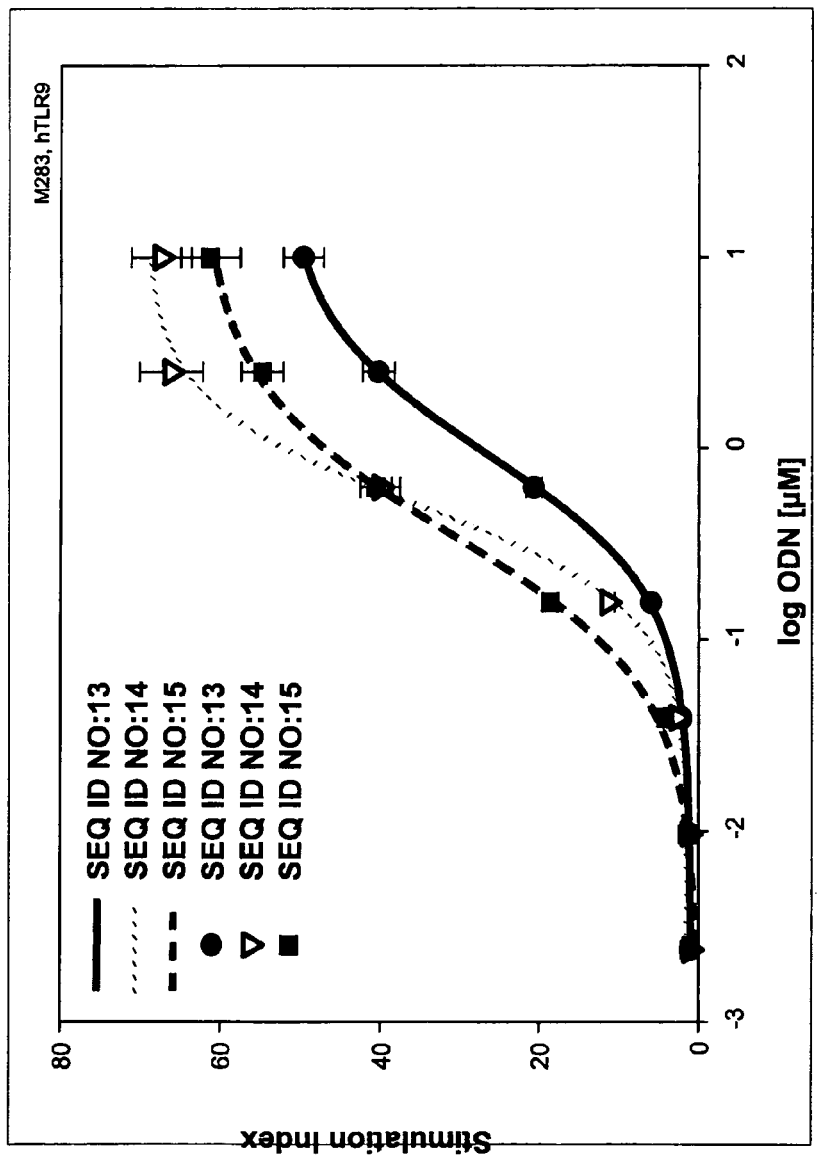
FIG. 3a shows a comparison of TLR9 stimulation by ODN of the same sequence, with a single CpG motif comprising a PS (SEQ ID NO:13), PO (SEQ ID NO:14), or PA (SEQ ID NO:15) modification in the backbone.

Phosphonoacetate Backbone Modification at the CpG Motif of B Class ODN Results in Increased TLR9 Activation Luciferase assays were performed to compare directly the effect of various backbone modifications in the CpG motif on TLR9 activation. ODN with identical sequence with PS (SEQ ID NO:13), PO (SEQ ID NO:14), or PA (SEQ ID NO:15) backbone modification at the one CpG motif were tested for the ability to activate TLR9 in TLR9-transfected HEK 293 cells. As shown in FIG. 3a, the ODN with the PA modification was a stronger TLR9 agonist than the ODN with the PS modification, although not quite as strong as the ODN with the PO modification.

Figure 3B:
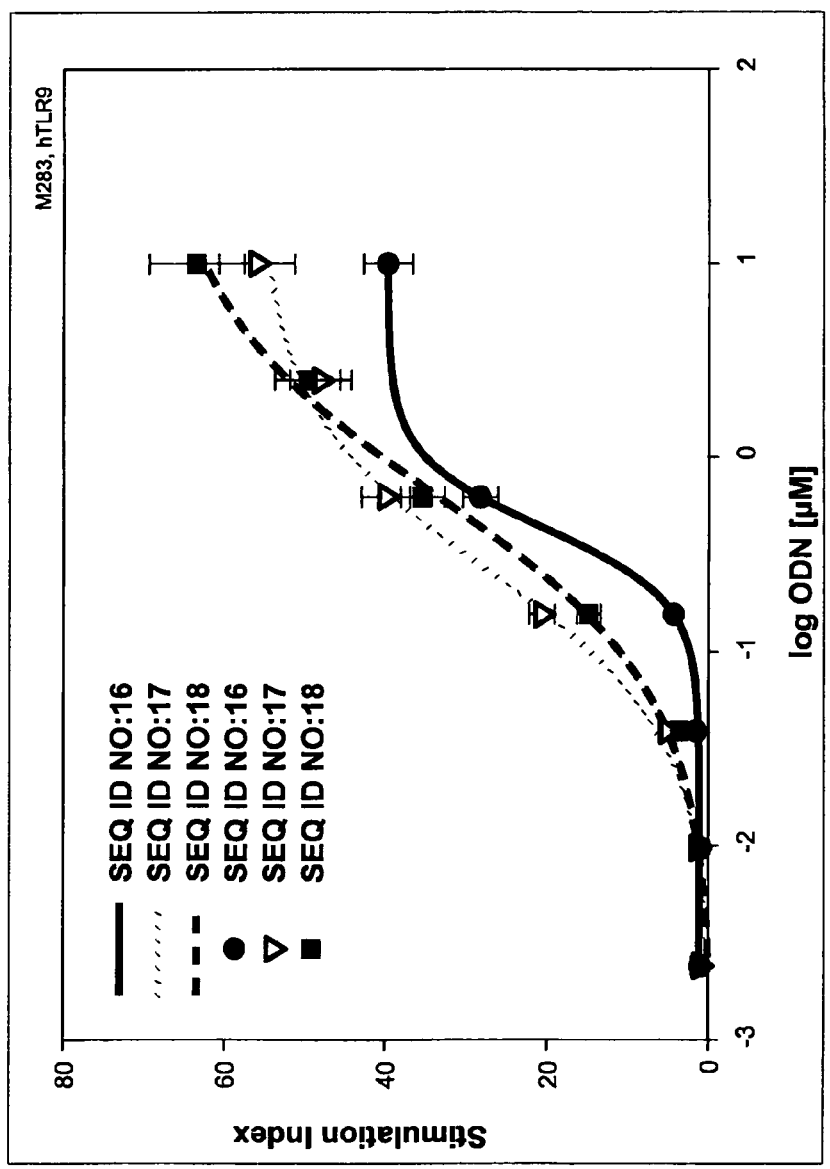
FIG. 3b shows a comparison of three ODN of the same sequence comprising two CpG motifs, in which each of the CpG motifs comprises either a PS or a PA backbone. ODN with either one (SEQ ID NO:17) or two (SEQ ID NO:18) PA modifications in a CpG motif were compared to stimulation by a PS oligonucleotide of the same sequence (SEQ ID NO:16).

A similar luciferase assay was performed with ODN that were either fully PS backbone (SEQ ID NO:16), had a PA modification at the first CpG motif (SEQ ID NO:17), or had a PA modification at both the first and second CpG motifs (SEQ ID NO:18). As shown in FIG. 3b, both ODN with PA modifications resulted in increased TLR9 activation over that resulting from the PS ODN. The ODN with modifications at two CpG motifs showed the most TLR9 activation.

Figure 3C:
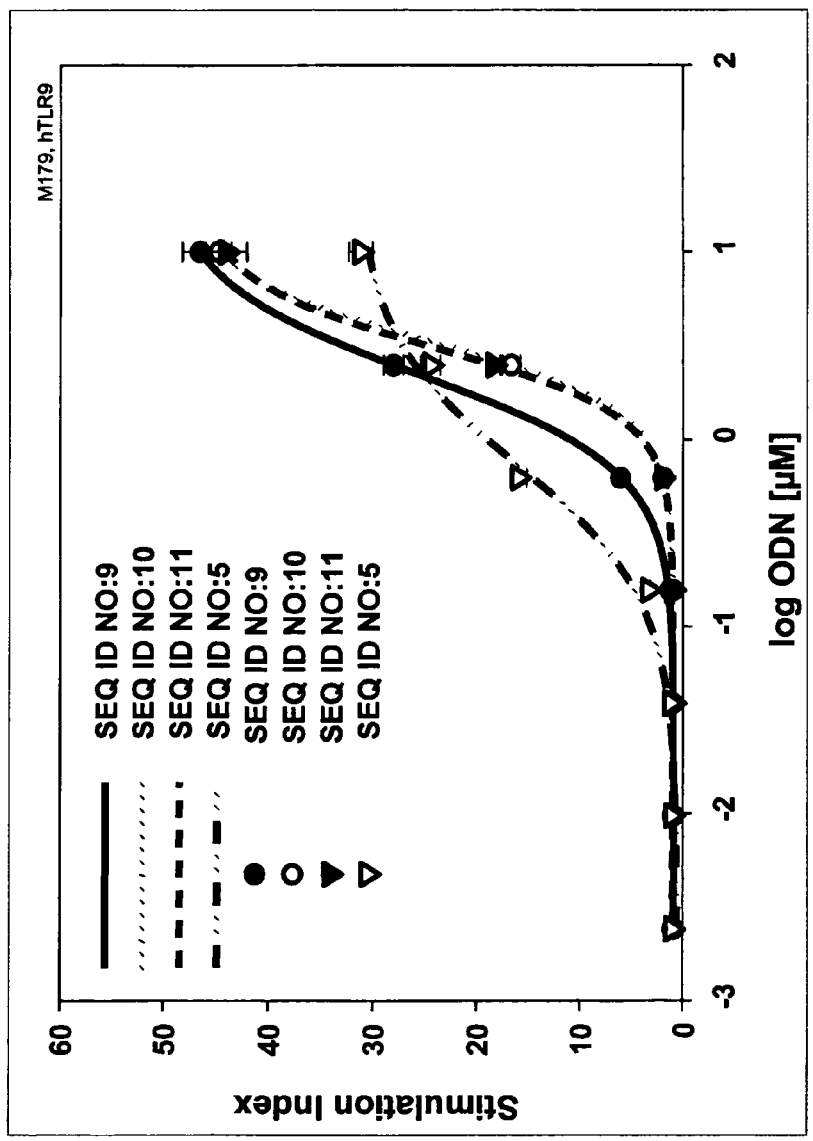
FIG. 3c shows TLR9 stimulation by ODN with the same sequence comprising multiple CpG motifs. Semi-soft ODN with either one (SEQ ID NO:9-10) or two (SEQ ID NO:11) PA modifications in a CpG motif were compared to stimulation by a PS oligonucleotide of the same sequence (SEQ ID NO:5). The y-axes are relative stimulation index and the x-axes are log ODN concentration in μM.

The same assay was performed to compare TLR9 activity induced by a fully phosphorothioate B class ODN (SEQ ID NO:5), a semi-soft B class ODN with one PA modification at first (most 5') CpG motif (SEQ ID NO:9), an ODN with one PA modification at the second CpG motif (SEQ ID NO:10) and an ODN wherein both CpG motifs are modified with a PA internucleotide linkage (SEQ ID NO:11). As shown in FIG. 3c, stimulation by all three PA-modified ODN resulted in an increase in TLR9 activation compared to SEQ ID NO:5. Table 3 summarizes the ODN tested.

TABLE 3

| Seq ID No. | Sequence | Description |
|---|---|---|
| 5 | T*C*G*T*C*G*T*T*T*G*C*G*T*C*G*T*T | B class PS |
| 9 | T*C<G*T*C-G*T*T*T-G*C-G*T*C-G*T*T | B class PA 1 |
| 10 | T*C-G*T*C<G*T*T*T-G*C-G*T*C-G*T*T | B class PA 2 |
| 11 | T*C<G*T*C<G*T*T*T-G*C-G*T*C-G*T*T | B class PA 1 & 2 |
| 13 | T*C*G*T*T*T*T*T*T*T*T*T*T*T*T*T*T*T | B class PS |
| 14 | T*C-G*T*T*T*T*T*T*T*T*T*T*T*T*T*T*T | B class PO |
| 15 | T*C<G*T*T*T*T*T*T*T*T*T*T*T*T*T*T*T | B class PA |
| 16 | T*C*G*T*C*G*T*T*T*T*T*T*T*T*T*T*T*T | B class PS |
| 17 | T*C<G*T*C*G*T*T*T*T*T*T*T*T*T*T*T*T | B class PA |
| 18 | T*C<G*T*C<G*T*T*T*T*T*T*T*T*T*T*T*T | B class PA x 2 |

< phosphonoacetate internucleotide linkage
* phosphorothioate internucleotide linkage
- phosphodiester internucleotide linkage Example 4

Figure 4:
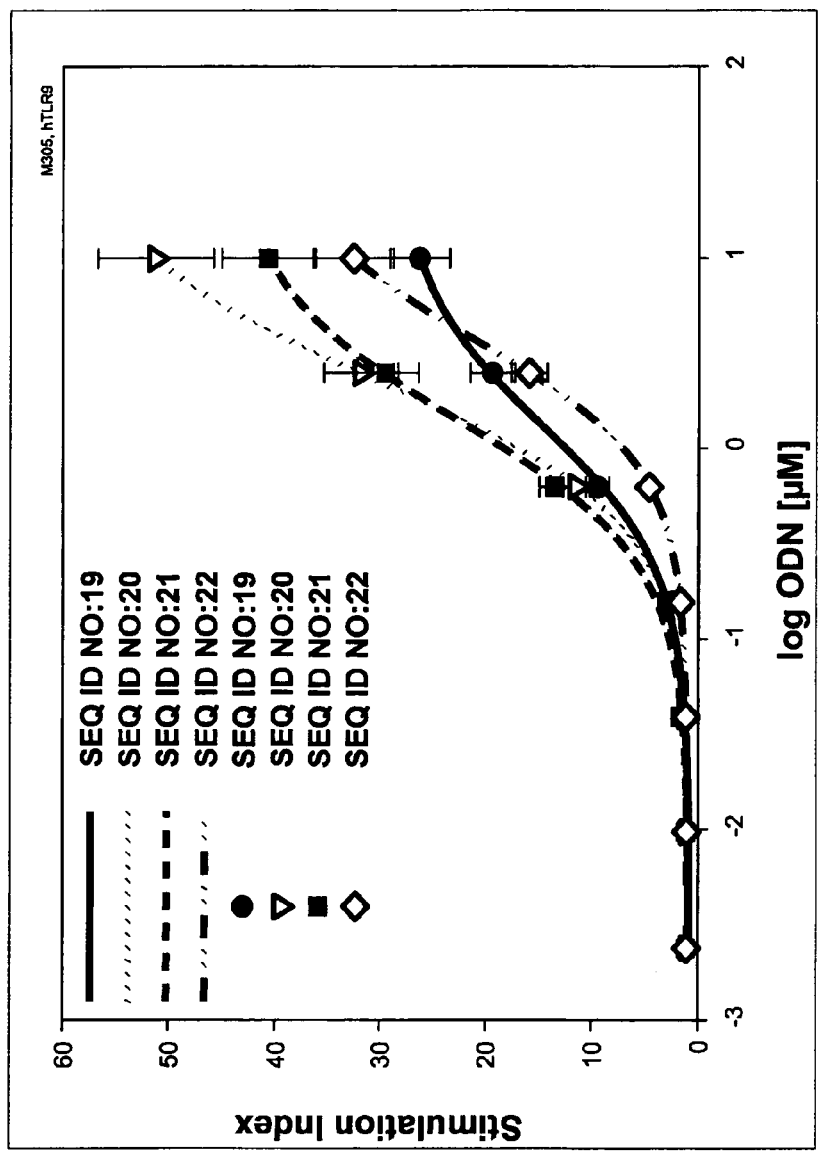
FIG. 4 is a graph showing TLR9 stimulation in TLR9-transfected HEK 293 cells following stimulation with semi-soft C class ODN of identical sequence but with varying backbone modifications at the CpG motifs, as measured by luciferase assay (SEQ ID NOs 19-22, see Table 4). The y-axis is stimulation index and the x-axis is the log of ODN concentration in μM.

Phosphonoacetate Backbone Modification at the CpG Motif of C Class ODN Results in Increased TLR9 Activation Phosphonoacetate-modified semi-soft C class ODN were tested for the ability to activate TLR9. TLR9-transfected HEK 293 of identical sequence, but with varying backbone modifications at the CpG motifs, were incubated with modified C class ODN and the resulting TLR9 activity was measured by luciferase assay. ODN with PA is modifications at varying positions were compared (see Table 4). FIG. 4 shows that the strongest activity was from ODN with PA or PO at the first (5') and second CpG motifs.

TABLE 4

| Seq ID No. | Sequence | Description |
|---|---|---|
| 19 | T*C*G*T*C<G*T*T*T*T*A*C-G*G*C*G*C*C- G*T*G*C*C*G-but | C class |
| 20 | T*C-G*T*C<G*T*T*T*T*A*C-G*G*C*G*C*C- G*T*G*C*C*G-but | C class |
| 21 | T*C<G*T*C-G*T*T*T*T*A*C-G*G*C*G*C*C- G*T*G*C*C*G-but | C class |
| 20 | T*C*G*T*C-G*T*T*T*T*A-C<G*G*C*G*C*C- G*T*G*C*C*G-but | C class |

< phosphonoacetate internucleotide linkage
* phosphorothioate internucleotide linkage
- phosphodiester internucleotide linkage
but butyrate Example 5

Figure 5A:
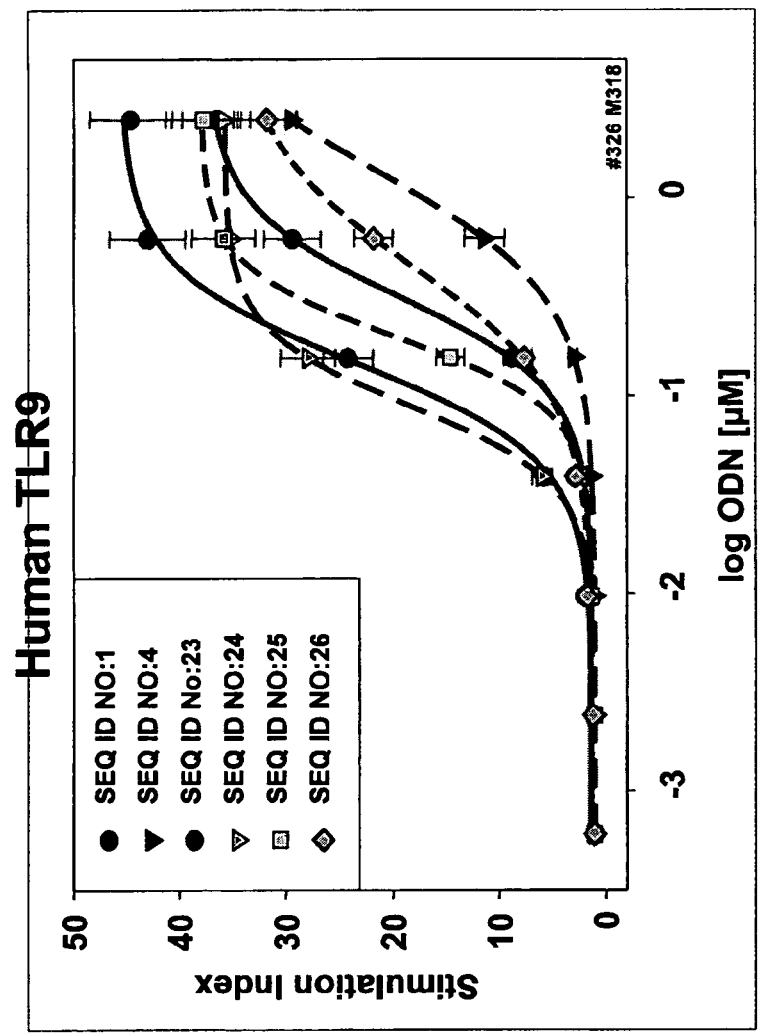
FIG. 5a compares the ability of four B class ODN (SEQ ID NOs 23-26, see Table 5) to stimulate TLR9 with PA modifications in different combinations of the four CpG motifs. A fully PS B class ODN (SEQ ID NO:1) and a C class ODN (SEQ ID NO: 4) were also tested.
Figure 5B:
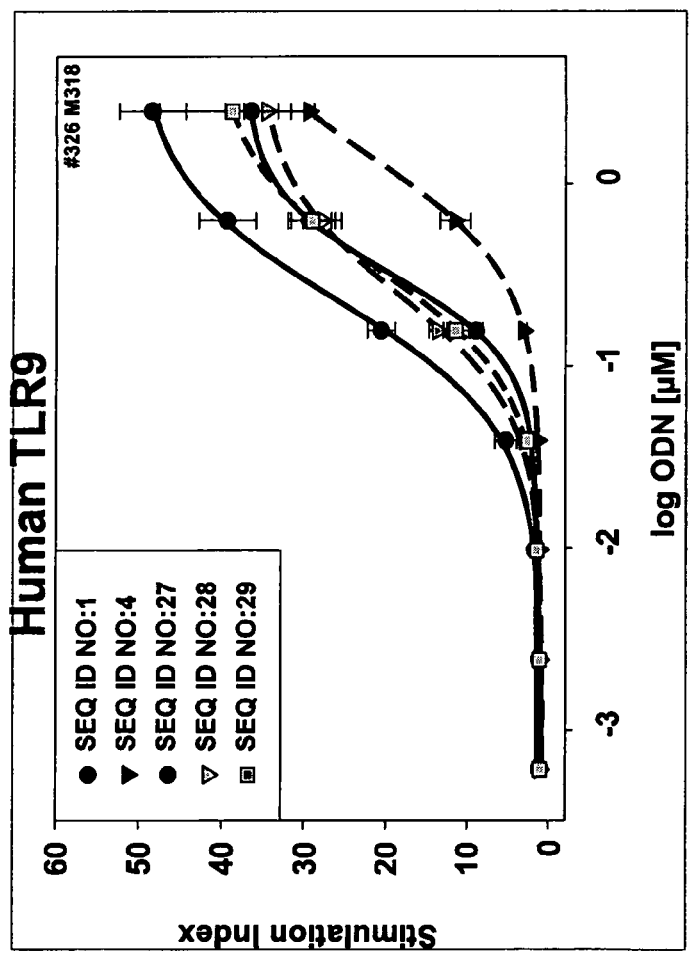
FIG. 5b compares the ability of three B class ODN (SEQ ID NOs 27-29, see Table 5) to stimulate TLR9 with PA modifications in different combinations of three CpG motifs. A fully PS B class ODN (SEQ ID NO:1) and a C class ODN (SEQ ID NO:4) were also tested.
Figure 5C:
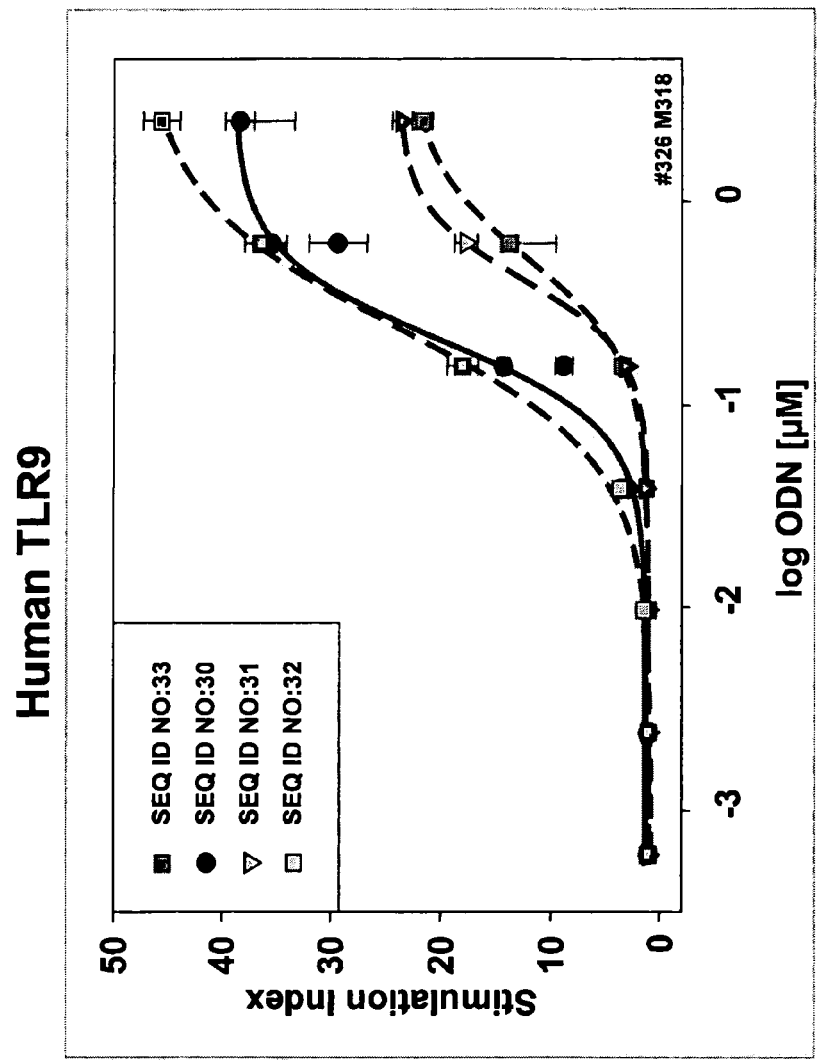
FIG. 5c shows a comparison of the ability of three C class ODN to stimulate TLR9 with PA modifications in either one (SEQ ID NOs:30-31) of two or both (SEQ ID NO:32) CpG motifs. A fully PS C class ODN of the same sequence was also tested (SEQ ID NO:33). The y-axes are relative stimulation index and the x-axes are log ODN concentration in μM.

Positioning of the Phosphonoacetate Backbone Modification Affects Potency and Efficacy To further investigate the effect of PA modification on the ability of ODN to activate TLR9, further modifications were made at the CpG motif of B class and C class ODN and tested for the ability to stimulate TLR9 in TLR9-transfected HEK 293 cells. B class ODN SEQ ID NO:1 was modified with a PA at the $1^{st}$ CpG motif (SEQ ID NO:23), the $2^{nd}$ CpG motif (SEQ ID NO:24), the $3^{rd}$ motif (SEQ ID NO:25) or the $4^{th}$ motif (SEQ to ID NO:26). As shown in FIG. 5a, PA modification at the $1^{st}$ CpG increased potency and efficacy of TLR9 dependent signal strength, and PA modification of the $2^{nd}$ and $3^{rd}$ CpG increased potency. PA modification at the $4^{th}$ CpG reduced both potency and efficacy.

SEQ ID NO:1 derivatives with more than one PA-modified CpG motif were then tested, wherein either the $1^{st}$ and $2^{nd}$ (SEQ ID NO:27), $2^{nd}$ and $4^{th}$ (SEQ ID NO:28) or $1^{st}$, $2^{nd}$, and $4^{th}$ (SEQ ID NO:29) CpG were modified. As shown in FIG.

5*b*, PA modification at the 1$^{st}$ and 2$^{nd}$ CpG increased potency and efficacy of TLR9 activation, whereas PA modification at the 2$^{nd}$ and 4$^{th}$ or 1$^{st}$, 2$^{nd}$ and 4$^{th}$ had minimal effect on potency and efficacy.

C class ODN SEQ ID NO:33 derivatives with a PA modification at different positions were also tested for the ability to activate TLR9. PA modification was made at the 1$^{st}$ CpG motif (SEQ ID NO:30), the 2$^{nd}$ CpG motif (SEQ ID NO:31), or both the 1$^{st}$ and 2$^{nd}$ CpG motif (SEQ ID NO:32). As shown in FIG. 5*c*, PA modification at the 1$^{st}$ or 1$^{st}$ and 2$^{nd}$ CpG increased potency and efficacy of TLR9 activation, whereas PA modification at the 2$^{nd}$ CpG alone did not influence potency and efficacy. Table 5 shows a summary of ODN tested. Taken together these data indicate that ODN with modification at least at the 1$^{st}$ CpG motif have resulted in the most potent TLR9 activation.

TABLE 5

| Seq ID No. | Sequence | Description |
|---|---|---|
| 1 | T*C*G*T*C*G*T*T*T*T*C*G*G*T*C*G*T*T*T*T | B class |
| 4 | T*C*G*T*C-G*T*T*T*A*C-G*G*C*G*C*C-G*T*G*C*C*G | C class |
| 23 | T*C<G*T*C*G*T*T*T*T*C*G*G*T*C*G*T*T*T*T | B class |
| 24 | T*C*G*T*C<G*T*T*T*T*C*G*G*T*C*G*T*T*T*T | B class |
| 25 | T*C*G*T*C*G*T*T*T*T*C<G*G*T*C*G*T*T*T*T | B class |
| 26 | T*C*G*T*C*G*T*T*T*T*C*G*G*T*C<G*T*T*T*T | B class |
| 27 | T*C<G*T*C<G*T*T*T*T*C*G*G*T*C*G*T*T*T*T | B class |
| 28 | T*C*G*T*C<G*T*T*T*T*C*G*G*T*C<G*T*T*T*T | B class |
| 29 | T*C<G*T*C<G*T*T*T*T*C*G*G*T*C<G*T*T*T*T | B class |
| 30 | T*C<G*T*C*G*T*T*T*T*C*G*G*C*G*C*G*C*G*C*C*3mG | C class |
| 31 | T*C*G*T*C<G*T*T*T*T*C*G*G*C*G*C*G*C*G*C*C*3mG | C class |
| 32 | T*C<G*T*C<G*T*T*T*T*C*G*G*C*G*C*G*C*G*C*C*3mG | C class |
| 33 | T*C*G*T*C*G*T*T*T*T*C*G*G*C*G*C*G*C*G*C*C*3mG | C class |

< PA internucleotide linkage
* PS internucleotide linkage
\- PO internucleotide linkage
3mG 3'-O-methyl-G

Equivalents

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within to the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

We claim:

1. An immunostimulatory oligonucleotide consisting of a TLR9 ligand having at least one unmethylated phosphate-modified CpG dinucleotide according to Formula I,

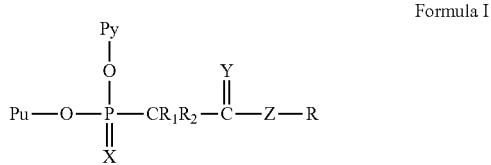

Formula I wherein:

R is selected from the group consisting of hydrogen (H), C1-C4-alkyl, methoxyethyl, pivaloyl oxymethyl, pivaloyl oxybenzyl, S-pivaloyl thioethyl and physiologically tolerated salts thereof;

X is independently oxygen (O) or sulfur (S);

Py is an unmethylated cytosine or modified cytosine nucleotide and Pu is an unmethylated guanine or modified guanine nucleotide; and Y and Z are independently oxygen (O) or sulfur (S) and R1 and R2 are independently H or C1-C4 alkyl and thus together give rise to a phosphonacetate or phosphonoacetate-like linkage between nucleotides;

further wherein the oligonucleotide is 7 to 100 nucleotides long and includes a chimeric backbone in which said phosphonoacetate or phosphonoacetate-like linkage between nucleotides is restricted to said at least one unmethylated phosphate-modified CpG dinucleotide.

2. The immunostimulatory oligonucleotide of claim 1, wherein the oligonucleotide further comprises second and third pyrimidine-purine dinucleotides, wherein the second pyrimidine-purine dinucleotide has a phosphodiester linkage or a phosphorothioate linkage and the third pyrimidine-purine dinucleotide has a phosphodiester linkage.

3. The immunostimulatory oligonucleotide of claim 1, wherein at least one nucleotide of the immunostimulatory oligonucleotide has a modified sugar residue 3'—O-alkyl-ribose.

4. A composition comprising: (a) a first oligonucleotide comprising the immunostimulatory oligonucleotide according to claim 1 and (b) at least one therapeutic agent, wherein the chimeric backbone of said immunostimulatory oligonucleotide is linked to said at least one therapeutic agent.

5. The composition of claim 4, wherein said at least one therapeutic agent is a second oligonucleotide, wherein said second oligonucleotide is linked to said first nucleotide to form to form a branched structure.

6. The composition of claim 4, wherein said at least one therapeutic agent is a second oligonucleotide, wherein said the second oligonucleotide is linked to said first nucleotide to form a 3'-3' linkage.

7. A composition comprising: (a) the immunostimulatory oligonucleotide according to claim 1 and (b) at least one therapeutic agent selected from the group consisting of an antigen, an antibacterial agent, an anticancer agent, an antiviral agent, an asthma or allergy medicament, and an autoimmune disease medicament.

8. A method of stimulating an immune response in a subject comprising the step of administering to the subject an amount of a composition effective to stimulate an immune response, the composition comprising the immunostimulatory oligonucleotide according to claim 1 having at least one phosphonoacetate or phosphonoacetate-like internucleotide linkage and a chimeric backbone formulated with a pharmaceutical carrier.

9. A method of treating an infection in a subject comprising the step of administering to the subject in need of such treatment a composition comprising an amount of the immunostimulatory oligonucleotide of claim 1 effective for treating the infection formulated with a pharmaceutical carrier.

10. A method of treating asthma in a subject comprising the step of administering to the subject in need of such treatment a composition comprising an amount of the immunostimulatory oligonucleotide of claim 1 effective for treating asthma formulated with a pharmaceutical carrier.

11. A method of treating allergy in a subject comprising the step of administering to the subject in need of such treatment a composition comprising an amount of the immunostimulatory oligonucleotide of claim 1 effective for treating allergy formulated with a pharmaceutical carrier.

* * * * *

SEQUENCE LISTING

```
<160> NUMBER OF SEQ ID NOS: 33

<210> SEQ ID NO 1
<211> LENGTH: 21
<212> TYPE: DNA
<213> ORGANISM: Artificial Sequence
<220> FEATURE:
<223> OTHER INFORMATION: B Class synthetic oligonucleotide
<220> FEATURE:
<221> NAME/KEY: misc_feature
<222> LOCATION: (1)..(21)
<223> OTHER INFORMATION: Phosphorothioate Internucleotide Linkages
```

<400> SEQUENCE: 1
tcgtcgtttt tcggtcgttt t                                              21

<210> SEQ ID NO 2
<211> LENGTH: 17
<212> TYPE: DNA
<213> ORGANISM: Artificial Sequence
<220> FEATURE:
<223> OTHER INFORMATION: B Class synthetic oligonucleotide
<220> FEATURE:
<221> NAME/KEY: misc_feature
<222> LOCATION: (1)..(2)
<223> OTHER INFORMATION: Phosphorothioate Internucleotide Linkages
<220> FEATURE:
<221> NAME/KEY: misc_feature
<222> LOCATION: (2)..(3)
<223> OTHER INFORMATION: Phosphodiester Internucleotide Linkages
<220> FEATURE:
<221> NAME/KEY: misc_feature
<222> LOCATION: (3)..(5)
<223> OTHER INFORMATION: Phosphorothioate Internucleotide Linkages
<220> FEATURE:
<221> NAME/KEY: misc_feature
<222> LOCATION: (5)..(6)
<223> OTHER INFORMATION: Phosphodiester Internucleotide Linkages
<220> FEATURE:
<221> NAME/KEY: misc_feature
<222> LOCATION: (6)..(9)
<223> OTHER INFORMATION: Phosphorothioate Internucleotide Linkages
<220> FEATURE:
<221> NAME/KEY: misc_feature
<222> LOCATION: (9)..(10)
<223> OTHER INFORMATION: Phosphodiester Internucleotide Linkages
<220> FEATURE:
<221> NAME/KEY: misc_feature
<222> LOCATION: (10)..(11)
<223> OTHER INFORMATION: Phosphorothioate Internucleotide Linkages
<220> FEATURE:
<221> NAME/KEY: misc_feature
<222> LOCATION: (11)..(12)
<223> OTHER INFORMATION: Phosphodiester Internucleotide Linkages
<220> FEATURE:
<221> NAME/KEY: misc_feature
<222> LOCATION: (12)..(14)
<223> OTHER INFORMATION: Phosphorothioate Internucleotide Linkages
<220> FEATURE:
<221> NAME/KEY: misc_feature
<222> LOCATION: (14)..(15)
<223> OTHER INFORMATION: Phosphodiester Internucleotide Linkages
<220> FEATURE:
<221> NAME/KEY: misc_feature
<222> LOCATION: (15)..(17)
<223> OTHER INFORMATION: Phosphorothioate Internucleotide Linkages

<400> SEQUENCE: 2
tcgtcgtttg cgtcgtt                                                   17

<210> SEQ ID NO 3
<211> LENGTH: 24
<212> TYPE: DNA
<213> ORGANISM: Artificial Sequence
<220> FEATURE:
<223> OTHER INFORMATION: B Class synthetic oligonucleotide
<220> FEATURE:
<221> NAME/KEY: misc_feature
<222> LOCATION: (1)..(2)
<223> OTHER INFORMATION: Phosphorothioate Internucleotide Linkages
<220> FEATURE:
<221> NAME/KEY: misc_feature
<222> LOCATION: (2)..(3)
<223> OTHER INFORMATION: Phosphodiester Internucleotide Linkages
<220> FEATURE:
<221> NAME/KEY: misc_feature
<222> LOCATION: (3)..(5)
<223> OTHER INFORMATION: Phosphorothioate Internucleotide Linkages -continued

```
<220> FEATURE:
<221> NAME/KEY: misc_feature
<222> LOCATION: (5)..(6)
<223> OTHER INFORMATION: Phosphodiester Internucleotide Linkages
<220> FEATURE:
<221> NAME/KEY: misc_feature
<222> LOCATION: (6)..(13)
<223> OTHER INFORMATION: Phosphorothioate Internucleotide Linkages
<220> FEATURE:
<221> NAME/KEY: misc_feature
<222> LOCATION: (13)..(14)
<223> OTHER INFORMATION: Phosphodiester Internucleotide Linkages
<220> FEATURE:
<221> NAME/KEY: misc_feature
<222> LOCATION: (14)..(21)
<223> OTHER INFORMATION: Phosphorothioate Internucleotide Linkages
<220> FEATURE:
<221> NAME/KEY: misc_feature
<222> LOCATION: (21)..(22)
<223> OTHER INFORMATION: Phosphodiester Internucleotide Linkages
<220> FEATURE:
<221> NAME/KEY: misc_feature
<222> LOCATION: (22)..(24)
<223> OTHER INFORMATION: Phosphorothioate Internucleotide Linkages

<400> SEQUENCE: 3
tcgtcgtttt gtcgttttgt cgtt                                              24

<210> SEQ ID NO 4
<211> LENGTH: 24
<212> TYPE: DNA
<213> ORGANISM: Artificial Sequence
<220> FEATURE:
<223> OTHER INFORMATION: C Class synthetic oligonucleotide
<220> FEATURE:
<221> NAME/KEY: misc_feature
<222> LOCATION: (1)..(5)
<223> OTHER INFORMATION: Phosphorothioate Internucleotide Linkages
<220> FEATURE:
<221> NAME/KEY: misc_feature
<222> LOCATION: (5)..(6)
<223> OTHER INFORMATION: Phosphodiester Internucleotide Linkages
<220> FEATURE:
<221> NAME/KEY: misc_feature
<222> LOCATION: (6)..(12)
<223> OTHER INFORMATION: Phosphorothioate Internucleotide Linkages
<220> FEATURE:
<221> NAME/KEY: misc_feature
<222> LOCATION: (12)..(13)
<223> OTHER INFORMATION: Phosphodiester Internucleotide Linkages
<220> FEATURE:
<221> NAME/KEY: misc_feature
<222> LOCATION: (13)..(18)
<223> OTHER INFORMATION: Phosphorothioate Internucleotide Linkages
<220> FEATURE:
<221> NAME/KEY: misc_feature
<222> LOCATION: (18)..(19)
<223> OTHER INFORMATION: Phosphodiester Internucleotide Linkages
<220> FEATURE:
<221> NAME/KEY: misc_feature
<222> LOCATION: (19)..(24)
<223> OTHER INFORMATION: Phosphorothioate Internucleotide Linkages

<400> SEQUENCE: 4
tcgtcgtttt acggcgccgt gccg                                              24

<210> SEQ ID NO 5
<211> LENGTH: 17
<212> TYPE: DNA
<213> ORGANISM: Artificial Sequence
<220> FEATURE:
<223> OTHER INFORMATION: B Class PS synthetic oligonucleotide
<220> FEATURE:
<221> NAME/KEY: misc_feature
<222> LOCATION: (1)..(17)
```

<223> OTHER INFORMATION: Phosphorothioate Internucleotide Linkages

<400> SEQUENCE: 5
tcgtcgtttg cgtcgtt                                                              17

<210> SEQ ID NO 6
<211> LENGTH: 20
<212> TYPE: DNA
<213> ORGANISM: Artificial Sequence
<220> FEATURE:
<223> OTHER INFORMATION: B Class PS synthetic oligonucleotide
<220> FEATURE:
<221> NAME/KEY: misc_feature
<222> LOCATION: (1)..(20)
<223> OTHER INFORMATION: Phosphorothioate Internucleotide Linkages

<400> SEQUENCE: 6
tgtcgttttt tttttttttt                                                           20

<210> SEQ ID NO 7
<211> LENGTH: 20
<212> TYPE: DNA
<213> ORGANISM: Artificial Sequence
<220> FEATURE:
<223> OTHER INFORMATION: B Class PO synthetic oligonucleotide
<220> FEATURE:
<221> NAME/KEY: misc_feature
<222> LOCATION: (1)..(4)
<223> OTHER INFORMATION: Phosphorothioate Internucleotide Linkages
<220> FEATURE:
<221> NAME/KEY: misc_feature
<222> LOCATION: (4)..(5)
<223> OTHER INFORMATION: Phosphodiester Internucleotide Linkage
<220> FEATURE:
<221> NAME/KEY: misc_feature
<222> LOCATION: (5)..(20)
<223> OTHER INFORMATION: Phosphorothioate Internucleotide Linkages

<400> SEQUENCE: 7
tgtcgttttt tttttttttt                                                           20

<210> SEQ ID NO 8
<211> LENGTH: 20
<212> TYPE: DNA
<213> ORGANISM: Artificial Sequence
<220> FEATURE:
<223> OTHER INFORMATION: B Class PA synthetic oligonucleotide
<220> FEATURE:
<221> NAME/KEY: misc_feature
<222> LOCATION: (1)..(4)
<223> OTHER INFORMATION: Phosphorothioate Internucleotide Linkages
<220> FEATURE:
<221> NAME/KEY: misc_feature
<222> LOCATION: (4)..(5)
<223> OTHER INFORMATION: Phosphonoacetate Internucleotide Linkage
<220> FEATURE:
<221> NAME/KEY: misc_feature
<222> LOCATION: (5)..(20)
<223> OTHER INFORMATION: Phosphorothioate Internucleotide Linkages

<400> SEQUENCE: 8
tgtcgttttt tttttttttt                                                           20

<210> SEQ ID NO 9
<211> LENGTH: 17
<212> TYPE: DNA
<213> ORGANISM: Artificial Sequence
<220> FEATURE:
<223> OTHER INFORMATION: B Class PA 1 synthetic oligonucleotide
<220> FEATURE:
<221> NAME/KEY: misc_feature

```
<222> LOCATION: (1)..(2)
<223> OTHER INFORMATION: Phosphorothioate Internucleotide Linkages
<220> FEATURE:
<221> NAME/KEY: misc_feature
<222> LOCATION: (2)..(3)
<223> OTHER INFORMATION: Phosphonoacetate Internucleotide Linkage
<220> FEATURE:
<221> NAME/KEY: misc_feature
<222> LOCATION: (3)..(5)
<223> OTHER INFORMATION: Phosphorothioate Internucleotide Linkages
<220> FEATURE:
<221> NAME/KEY: misc_feature
<222> LOCATION: (5)..(6)
<223> OTHER INFORMATION: Phosphodiester Internucleotide Linkage
<220> FEATURE:
<221> NAME/KEY: misc_feature
<222> LOCATION: (6)..(9)
<223> OTHER INFORMATION: Phosphorothioate Internucleotide Linkages
<220> FEATURE:
<221> NAME/KEY: misc_feature
<222> LOCATION: (9)..(10)
<223> OTHER INFORMATION: Phosphodiester Internucleotide Linkage
<220> FEATURE:
<221> NAME/KEY: misc_feature
<222> LOCATION: (10)..(11)
<223> OTHER INFORMATION: Phosphorothioate Internucleotide Linkages
<220> FEATURE:
<221> NAME/KEY: misc_feature
<222> LOCATION: (11)..(12)
<223> OTHER INFORMATION: Phosphodiester Internucleotide Linkage
<220> FEATURE:
<221> NAME/KEY: misc_feature
<222> LOCATION: (12)..(14)
<223> OTHER INFORMATION: Phosphorothioate Internucleotide Linkages
<220> FEATURE:
<221> NAME/KEY: misc_feature
<222> LOCATION: (14)..(15)
<223> OTHER INFORMATION: Phosphodiester Internucleotide Linkage
<220> FEATURE:
<221> NAME/KEY: misc_feature
<222> LOCATION: (15)..(17)
<223> OTHER INFORMATION: Phosphorothioate Internucleotide Linkages

<400> SEQUENCE: 9
tcgtcgtttg cgtcgtt                                                    17

<210> SEQ ID NO 10
<211> LENGTH: 17
<212> TYPE: DNA
<213> ORGANISM: Artificial Sequence
<220> FEATURE:
<223> OTHER INFORMATION: B Class PA 2 synthetic oligonucleotide
<220> FEATURE:
<221> NAME/KEY: misc_feature
<222> LOCATION: (1)..(2)
<223> OTHER INFORMATION: Phosphorothioate Internucleotide Linkages
<220> FEATURE:
<221> NAME/KEY: misc_feature
<222> LOCATION: (2)..(3)
<223> OTHER INFORMATION: Phosphodiester Internucleotide Linkage
<220> FEATURE:
<221> NAME/KEY: misc_feature
<222> LOCATION: (3)..(5)
<223> OTHER INFORMATION: Phosphorothioate Internucleotide Linkages
<220> FEATURE:
<221> NAME/KEY: misc_feature
<222> LOCATION: (5)..(6)
<223> OTHER INFORMATION: Phosphonoacetate Internucleotide Linkage
<220> FEATURE:
<221> NAME/KEY: misc_feature
<222> LOCATION: (6)..(9)
<223> OTHER INFORMATION: Phosphorothioate Internucleotide Linkages
<220> FEATURE:
<221> NAME/KEY: misc_feature
<222> LOCATION: (9)..(10)
<223> OTHER INFORMATION: Phosphodiester Internucleotide Linkage
<220> FEATURE:
```

```
<221> NAME/KEY: misc_feature
<222> LOCATION: (10)..(11)
<223> OTHER INFORMATION: Phosphorothioate Internucleotide Linkages
<220> FEATURE:
<221> NAME/KEY: misc_feature
<222> LOCATION: (11)..(12)
<223> OTHER INFORMATION: Phosphodiester Internucleotide Linkage
<220> FEATURE:
<221> NAME/KEY: misc_feature
<222> LOCATION: (12)..(14)
<223> OTHER INFORMATION: Phosphorothioate Internucleotide Linkages
<220> FEATURE:
<221> NAME/KEY: misc_feature
<222> LOCATION: (14)..(15)
<223> OTHER INFORMATION: Phosphodiester Internucleotide Linkage
<220> FEATURE:
<221> NAME/KEY: misc_feature
<222> LOCATION: (15)..(17)
<223> OTHER INFORMATION: Phosphorothioate Internucleotide Linkages

<400> SEQUENCE: 10
tcgtcgtttg cgtcgtt                                                17

<210> SEQ ID NO 11
<211> LENGTH: 17
<212> TYPE: DNA
<213> ORGANISM: Artificial Sequence
<220> FEATURE:
<223> OTHER INFORMATION: B Class PA 1&2 synthetic oligonucleotide
<220> FEATURE:
<221> NAME/KEY: misc_feature
<222> LOCATION: (1)..(2)
<223> OTHER INFORMATION: Phosphorothioate Internucleotide Linkages
<220> FEATURE:
<221> NAME/KEY: misc_feature
<222> LOCATION: (2)..(3)
<223> OTHER INFORMATION: Phosphonoacetate Internucleotide Linkage
<220> FEATURE:
<221> NAME/KEY: misc_feature
<222> LOCATION: (3)..(5)
<223> OTHER INFORMATION: Phosphorothioate Internucleotide Linkages
<220> FEATURE:
<221> NAME/KEY: misc_feature
<222> LOCATION: (5)..(6)
<223> OTHER INFORMATION: Phosphonoacetate Internucleotide Linkage
<220> FEATURE:
<221> NAME/KEY: misc_feature
<222> LOCATION: (6)..(9)
<223> OTHER INFORMATION: Phosphorothioate Internucleotide Linkages
<220> FEATURE:
<221> NAME/KEY: misc_feature
<222> LOCATION: (9)..(10)
<223> OTHER INFORMATION: Phosphodiester Internucleotide Linkage
<220> FEATURE:
<221> NAME/KEY: misc_feature
<222> LOCATION: (10)..(11)
<223> OTHER INFORMATION: Phosphorothioate Internucleotide Linkages
<220> FEATURE:
<221> NAME/KEY: misc_feature
<222> LOCATION: (11)..(12)
<223> OTHER INFORMATION: Phosphodiester Internucleotide Linkage
<220> FEATURE:
<221> NAME/KEY: misc_feature
<222> LOCATION: (12)..(14)
<223> OTHER INFORMATION: Phosphorothioate Internucleotide Linkages
<220> FEATURE:
<221> NAME/KEY: misc_feature
<222> LOCATION: (14)..(15)
<223> OTHER INFORMATION: Phosphodiester Internucleotide Linkage
<220> FEATURE:
<221> NAME/KEY: misc_feature
<222> LOCATION: (15)..(17)
<223> OTHER INFORMATION: Phosphorothioate Internucleotide Linkages

<400> SEQUENCE: 11
tcgtcgtttg cgtcgtt                                                17
```

```
<210> SEQ ID NO 12
<211> LENGTH: 20
<212> TYPE: DNA
<213> ORGANISM: Artificial Sequence
<220> FEATURE:
<223> OTHER INFORMATION: B Class P-Me synthetic oligonucleotide
<220> FEATURE:
<221> NAME/KEY: misc_feature
<222> LOCATION: (1)..(4)
<223> OTHER INFORMATION: Phosphorothioate Internucleotide Linkages
<220> FEATURE:
<221> NAME/KEY: misc_feature
<222> LOCATION: (4)..(5)
<223> OTHER INFORMATION: Methyl-phosphonate Internucleotide Linkage
<220> FEATURE:
<221> NAME/KEY: misc_feature
<222> LOCATION: (5)..(20)
<223> OTHER INFORMATION: Phosphorothioate Internucleotide Linkages

<400> SEQUENCE: 12
tgtcgttttt tttttttttt                                           20

<210> SEQ ID NO 13
<211> LENGTH: 20
<212> TYPE: DNA
<213> ORGANISM: Artificial Sequence
<220> FEATURE:
<223> OTHER INFORMATION: B Class PS synthetic oligonucleotide
<220> FEATURE:
<221> NAME/KEY: misc_feature
<222> LOCATION: (1)..(20)
<223> OTHER INFORMATION: Phosphorothioate Internucleotide Linkages

<400> SEQUENCE: 13
tcgttttttt tttttttttt                                           20

<210> SEQ ID NO 14
<211> LENGTH: 20
<212> TYPE: DNA
<213> ORGANISM: Artificial Sequence
<220> FEATURE:
<223> OTHER INFORMATION: B Class PO synthetic oligonucleotide
<220> FEATURE:
<221> NAME/KEY: misc_feature
<222> LOCATION: (1)..(2)
<223> OTHER INFORMATION: Phosphorothioate Internucleotide Linkages
<220> FEATURE:
<221> NAME/KEY: misc_feature
<222> LOCATION: (2)..(3)
<223> OTHER INFORMATION: Phosphodiester Internucleotide Linkage
<220> FEATURE:
<221> NAME/KEY: misc_feature
<222> LOCATION: (3)..(20)
<223> OTHER INFORMATION: Phosphorothioate Internucleotide Linkages

<400> SEQUENCE: 14
tcgttttttt tttttttttt                                           20

<210> SEQ ID NO 15
<211> LENGTH: 20
<212> TYPE: DNA
<213> ORGANISM: Artificial Sequence
<220> FEATURE:
<223> OTHER INFORMATION: B Class PA synthetic oligonucleotide
<220> FEATURE:
<221> NAME/KEY: misc_feature
<222> LOCATION: (1)..(2)
<223> OTHER INFORMATION: Phosphorothioate Internucleotide Linkages
<220> FEATURE:
<221> NAME/KEY: misc_feature
<222> LOCATION: (2)..(3)
```

```
<223> OTHER INFORMATION: Phosphonoacetate Internucleotide Linkage
<220> FEATURE:
<221> NAME/KEY: misc_feature
<222> LOCATION: (3)..(20)
<223> OTHER INFORMATION: Phosphorothioate Internucleotide Linkages

<400> SEQUENCE: 15
tcgttttttt tttttttttt                                                    20

<210> SEQ ID NO 16
<211> LENGTH: 20
<212> TYPE: DNA
<213> ORGANISM: Artificial Sequence
<220> FEATURE:
<223> OTHER INFORMATION: B Class PS synthetic oligonucleotide
<220> FEATURE:
<221> NAME/KEY: misc_feature
<222> LOCATION: (1)..(20)
<223> OTHER INFORMATION: Phosphorothioate Internucleotide Linkages

<400> SEQUENCE: 16
tcgtcgtttt tttttttttt                                                    20

<210> SEQ ID NO 17
<211> LENGTH: 20
<212> TYPE: DNA
<213> ORGANISM: Artificial Sequence
<220> FEATURE:
<223> OTHER INFORMATION: B Class PA synthetic oligonucleotide
<220> FEATURE:
<221> NAME/KEY: misc_feature
<222> LOCATION: (1)..(2)
<223> OTHER INFORMATION: Phosphorothioate Internucleotide Linkages
<220> FEATURE:
<221> NAME/KEY: misc_feature
<222> LOCATION: (2)..(3)
<223> OTHER INFORMATION: Phosphonoacetate Internucleotide Linkage
<220> FEATURE:
<221> NAME/KEY: misc_feature
<222> LOCATION: (3)..(20)
<223> OTHER INFORMATION: Phosphorothioate Internucleotide Linkages

<400> SEQUENCE: 17
tcgtcgtttt tttttttttt                                                    20

<210> SEQ ID NO 18
<211> LENGTH: 20
<212> TYPE: DNA
<213> ORGANISM: Artificial Sequence
<220> FEATURE:
<223> OTHER INFORMATION: B Class PA x 2 synthetic oligonucleotide
<220> FEATURE:
<221> NAME/KEY: misc_feature
<222> LOCATION: (1)..(2)
<223> OTHER INFORMATION: Phosphorothioate Internucleotide Linkages
<220> FEATURE:
<221> NAME/KEY: misc_feature
<222> LOCATION: (2)..(3)
<223> OTHER INFORMATION: Phosphonoacetate Internucleotide Linkage
<220> FEATURE:
<221> NAME/KEY: misc_feature
<222> LOCATION: (3)..(5)
<223> OTHER INFORMATION: Phosphorothioate Internucleotide Linkages
<220> FEATURE:
<221> NAME/KEY: misc_feature
<222> LOCATION: (5)..(6)
<223> OTHER INFORMATION: Phosphonoacetate Internucleotide Linkage
<220> FEATURE:
<221> NAME/KEY: misc_feature
<222> LOCATION: (6)..(20)
<223> OTHER INFORMATION: Phosphorothioate Internucleotide Linkages

<400> SEQUENCE: 18
```
tcgtcgtttt tttttttttt                                    20

<210> SEQ ID NO 19
<211> LENGTH: 24
<212> TYPE: DNA
<213> ORGANISM: Artificial Sequence
<220> FEATURE:
<223> OTHER INFORMATION: C Class synthetic oligonucleotide
<220> FEATURE:
<221> NAME/KEY: misc_feature
<222> LOCATION: (1)..(5)
<223> OTHER INFORMATION: Phosphorothioate Internucleotide Linkages
<220> FEATURE:
<221> NAME/KEY: misc_feature
<222> LOCATION: (5)..(6)
<223> OTHER INFORMATION: Phosphonoacetate Internucleotide Linkage
<220> FEATURE:
<221> NAME/KEY: misc_feature
<222> LOCATION: (6)..(12)
<223> OTHER INFORMATION: Phosphorothioate Internucleotide Linkages
<220> FEATURE:
<221> NAME/KEY: misc_feature
<222> LOCATION: (12)..(13)
<223> OTHER INFORMATION: Phosphodiester Internucleotide Linkages
<220> FEATURE:
<221> NAME/KEY: misc_feature
<222> LOCATION: (13)..(18)
<223> OTHER INFORMATION: Phosphorothioate Internucleotide Linkages
<220> FEATURE:
<221> NAME/KEY: misc_feature
<222> LOCATION: (18)..(19)
<223> OTHER INFORMATION: Phosphodiester Internucleotide Linkages
<220> FEATURE:
<221> NAME/KEY: misc_feature
<222> LOCATION: (19)..(24)
<223> OTHER INFORMATION: Phosphorothioate Internucleotide Linkages

<400> SEQUENCE: 19
tcgtcgtttt acggcgccgt gccg                                24

<210> SEQ ID NO 20
<211> LENGTH: 24
<212> TYPE: DNA
<213> ORGANISM: Artificial Sequence
<220> FEATURE:
<223> OTHER INFORMATION: C Class synthetic oligonucleotide
<220> FEATURE:
<221> NAME/KEY: misc_feature
<222> LOCATION: (1)..(2)
<223> OTHER INFORMATION: Phosphorothioate Internucleotide Linkages
<220> FEATURE:
<221> NAME/KEY: misc_feature
<222> LOCATION: (2)..(3)
<223> OTHER INFORMATION: Phosphodiester Internucleotide Linkages
<220> FEATURE:
<221> NAME/KEY: misc_feature
<222> LOCATION: (3)..(5)
<223> OTHER INFORMATION: Phosphorothioate Internucleotide Linkages
<220> FEATURE:
<221> NAME/KEY: misc_feature
<222> LOCATION: (5)..(6)
<223> OTHER INFORMATION: Phosphonoacetate Internucleotide Linkage
<220> FEATURE:
<221> NAME/KEY: misc_feature
<222> LOCATION: (6)..(12)
<223> OTHER INFORMATION: Phosphorothioate Internucleotide Linkages
<220> FEATURE:
<221> NAME/KEY: misc_feature
<222> LOCATION: (12)..(13)
<223> OTHER INFORMATION: Phosphodiester Internucleotide Linkages
<220> FEATURE:
<221> NAME/KEY: misc_feature
<222> LOCATION: (13)..(18)
<223> OTHER INFORMATION: Phosphorothioate Internucleotide Linkages
<220> FEATURE:

<221> NAME/KEY: misc_feature
<222> LOCATION: (18)..(19)
<223> OTHER INFORMATION: Phosphodiester Internucleotide Linkages
<220> FEATURE:
<221> NAME/KEY: misc_feature
<222> LOCATION: (19)..(24)
<223> OTHER INFORMATION: Phosphorothioate Internucleotide Linkages

<400> SEQUENCE: 20
tcgtcgtttt acggcgccgt gccg        24

<210> SEQ ID NO 21
<211> LENGTH: 24
<212> TYPE: DNA
<213> ORGANISM: Artificial Sequence
<220> FEATURE:
<223> OTHER INFORMATION: C Class synthetic oligonucleotide
<220> FEATURE:
<221> NAME/KEY: misc_feature
<222> LOCATION: (1)..(2)
<223> OTHER INFORMATION: Phosphorothioate Internucleotide Linkages
<220> FEATURE:
<221> NAME/KEY: misc_feature
<222> LOCATION: (2)..(3)
<223> OTHER INFORMATION: Phosphonoacetate Internucleotide Linkage
<220> FEATURE:
<221> NAME/KEY: misc_feature
<222> LOCATION: (3)..(5)
<223> OTHER INFORMATION: Phosphorothioate Internucleotide Linkages
<220> FEATURE:
<221> NAME/KEY: misc_feature
<222> LOCATION: (5)..(6)
<223> OTHER INFORMATION: Phosphodiester Internucleotide Linkages
<220> FEATURE:
<221> NAME/KEY: misc_feature
<222> LOCATION: (6)..(12)
<223> OTHER INFORMATION: Phosphorothioate Internucleotide Linkages
<220> FEATURE:
<221> NAME/KEY: misc_feature
<222> LOCATION: (12)..(13)
<223> OTHER INFORMATION: Phosphodiester Internucleotide Linkages
<220> FEATURE:
<221> NAME/KEY: misc_feature
<222> LOCATION: (13)..(18)
<223> OTHER INFORMATION: Phosphorothioate Internucleotide Linkages
<220> FEATURE:
<221> NAME/KEY: misc_feature
<222> LOCATION: (18)..(19)
<223> OTHER INFORMATION: Phosphodiester Internucleotide Linkages
<220> FEATURE:
<221> NAME/KEY: misc_feature
<222> LOCATION: (19)..(24)
<223> OTHER INFORMATION: Phosphorothioate Internucleotide Linkages

<400> SEQUENCE: 21
tcgtcgtttt acggcgccgt gccg        24

<210> SEQ ID NO 22
<211> LENGTH: 24
<212> TYPE: DNA
<213> ORGANISM: Artificial Sequence
<220> FEATURE:
<223> OTHER INFORMATION: C Class synthetic oligonucleotide
<220> FEATURE:
<221> NAME/KEY: misc_feature
<222> LOCATION: (1)..(5)
<223> OTHER INFORMATION: Phosphorothioate Internucleotide Linkages
<220> FEATURE:
<221> NAME/KEY: misc_feature
<222> LOCATION: (5)..(6)
<223> OTHER INFORMATION: Phosphodiester Internucleotide Linkages
<220> FEATURE:
<221> NAME/KEY: misc_feature
<222> LOCATION: (6)..(11)
<223> OTHER INFORMATION: Phosphorothioate Internucleotide Linkages

```
<220> FEATURE:
<221> NAME/KEY: misc_feature
<222> LOCATION: (11)..(12)
<223> OTHER INFORMATION: Phosphodiester Internucleotide Linkages
<220> FEATURE:
<221> NAME/KEY: misc_feature
<222> LOCATION: (12)..(13)
<223> OTHER INFORMATION: Phosphonoacetate Internucleotide Linkage
<220> FEATURE:
<221> NAME/KEY: misc_feature
<222> LOCATION: (13)..(18)
<223> OTHER INFORMATION: Phosphorothioate Internucleotide Linkages
<220> FEATURE:
<221> NAME/KEY: misc_feature
<222> LOCATION: (18)..(19)
<223> OTHER INFORMATION: Phosphodiester Internucleotide Linkages
<220> FEATURE:
<221> NAME/KEY: misc_feature
<222> LOCATION: (19)..(24)
<223> OTHER INFORMATION: Phosphorothioate Internucleotide Linkages

<400> SEQUENCE: 22
tcgtcgtttt acggcgccgt gccg                                          24

<210> SEQ ID NO 23
<211> LENGTH: 21
<212> TYPE: DNA
<213> ORGANISM: Artificial Sequence
<220> FEATURE:
<223> OTHER INFORMATION: B Class synthetic oligonucleotide
<220> FEATURE:
<221> NAME/KEY: misc_feature
<222> LOCATION: (1)..(2)
<223> OTHER INFORMATION: Phosphorothioate Internucleotide Linkages
<220> FEATURE:
<221> NAME/KEY: misc_feature
<222> LOCATION: (2)..(3)
<223> OTHER INFORMATION: Phosphonoacetate Internucleotide Linkage
<220> FEATURE:
<221> NAME/KEY: misc_feature
<222> LOCATION: (3)..(21)
<223> OTHER INFORMATION: Phosphorothioate Internucleotide Linkages

<400> SEQUENCE: 23
tcgtcgtttt tcggtcgttt t                                             21

<210> SEQ ID NO 24
<211> LENGTH: 21
<212> TYPE: DNA
<213> ORGANISM: Artificial Sequence
<220> FEATURE:
<223> OTHER INFORMATION: B Class synthetic oligonucleotide
<220> FEATURE:
<221> NAME/KEY: misc_feature
<222> LOCATION: (1)..(5)
<223> OTHER INFORMATION: Phosphorothioate Internucleotide Linkages
<220> FEATURE:
<221> NAME/KEY: misc_feature
<222> LOCATION: (5)..(6)
<223> OTHER INFORMATION: Phosphonoacetate Internucleotide Linkage
<220> FEATURE:
<221> NAME/KEY: misc_feature
<222> LOCATION: (6)..(21)
<223> OTHER INFORMATION: Phosphorothioate Internucleotide Linkages

<400> SEQUENCE: 24
tcgtcgtttt tcggtcgttt t                                             21

<210> SEQ ID NO 25
<211> LENGTH: 21
<212> TYPE: DNA
<213> ORGANISM: Artificial Sequence
<220> FEATURE:
```

```
<223> OTHER INFORMATION: B Class synthetic oligonucleotide
<220> FEATURE:
<221> NAME/KEY: misc_feature
<222> LOCATION: (1)..(12)
<223> OTHER INFORMATION: Phosphorothioate Internucleotide Linkages
<220> FEATURE:
<221> NAME/KEY: misc_feature
<222> LOCATION: (12)..(13)
<223> OTHER INFORMATION: Phosphonoacetate Internucleotide Linkage
<220> FEATURE:
<221> NAME/KEY: misc_feature
<222> LOCATION: (13)..(21)
<223> OTHER INFORMATION: Phosphorothioate Internucleotide Linkages

<400> SEQUENCE: 25
tcgtcgtttt tcggtcgttt t                                                21

<210> SEQ ID NO 26
<211> LENGTH: 21
<212> TYPE: DNA
<213> ORGANISM: Artificial Sequence
<220> FEATURE:
<223> OTHER INFORMATION: B Class synthetic oligonucleotide
<220> FEATURE:
<221> NAME/KEY: misc_feature
<222> LOCATION: (1)..(16)
<223> OTHER INFORMATION: Phosphorothioate Internucleotide Linkages
<220> FEATURE:
<221> NAME/KEY: misc_feature
<222> LOCATION: (16)..(17)
<223> OTHER INFORMATION: Phosphonoacetate Internucleotide Linkage
<220> FEATURE:
<221> NAME/KEY: misc_feature
<222> LOCATION: (17)..(21)
<223> OTHER INFORMATION: Phosphorothioate Internucleotide Linkages

<400> SEQUENCE: 26
tcgtcgtttt tcggtcgttt t                                                21

<210> SEQ ID NO 27
<211> LENGTH: 21
<212> TYPE: DNA
<213> ORGANISM: Artificial Sequence
<220> FEATURE:
<223> OTHER INFORMATION: B Class synthetic oligonucleotide
<220> FEATURE:
<221> NAME/KEY: misc_feature
<222> LOCATION: (1)..(2)
<223> OTHER INFORMATION: Phosphorothioate Internucleotide Linkages
<220> FEATURE:
<221> NAME/KEY: misc_feature
<222> LOCATION: (2)..(3)
<223> OTHER INFORMATION: Phosphonoacetate Internucleotide Linkage
<220> FEATURE:
<221> NAME/KEY: misc_feature
<222> LOCATION: (3)..(5)
<223> OTHER INFORMATION: Phosphorothioate Internucleotide Linkages
<220> FEATURE:
<221> NAME/KEY: misc_feature
<222> LOCATION: (5)..(6)
<223> OTHER INFORMATION: Phosphonoacetate Internucleotide Linkage
<220> FEATURE:
<221> NAME/KEY: misc_feature
<222> LOCATION: (6)..(21)
<223> OTHER INFORMATION: Phosphorothioate Internucleotide Linkages

<400> SEQUENCE: 27
tcgtcgtttt tcggtcgttt t                                                21

<210> SEQ ID NO 28
<211> LENGTH: 21
<212> TYPE: DNA
<213> ORGANISM: Artificial Sequence
```

```
<220> FEATURE:
<223> OTHER INFORMATION: B Class synthetic oligonucleotide
<220> FEATURE:
<221> NAME/KEY: misc_feature
<222> LOCATION: (1)..(5)
<223> OTHER INFORMATION: Phosphorothioate Internucleotide Linkages
<220> FEATURE:
<221> NAME/KEY: misc_feature
<222> LOCATION: (5)..(6)
<223> OTHER INFORMATION: Phosphonoacetate Internucleotide Linkage
<220> FEATURE:
<221> NAME/KEY: misc_feature
<222> LOCATION: (6)..(16)
<223> OTHER INFORMATION: Phosphorothioate Internucleotide Linkages
<220> FEATURE:
<221> NAME/KEY: misc_feature
<222> LOCATION: (16)..(17)
<223> OTHER INFORMATION: Phosphonoacetate Internucleotide Linkage
<220> FEATURE:
<221> NAME/KEY: misc_feature
<222> LOCATION: (17)..(21)
<223> OTHER INFORMATION: Phosphorothioate Internucleotide Linkages

<400> SEQUENCE: 28
tcgtcgtttt tcggtcgttt t                                             21

<210> SEQ ID NO 29
<211> LENGTH: 21
<212> TYPE: DNA
<213> ORGANISM: Artificial Sequence
<220> FEATURE:
<223> OTHER INFORMATION: B Class synthetic oligonucleotide
<220> FEATURE:
<221> NAME/KEY: misc_feature
<222> LOCATION: (1)..(2)
<223> OTHER INFORMATION: Phosphorothioate Internucleotide Linkages
<220> FEATURE:
<221> NAME/KEY: misc_feature
<222> LOCATION: (2)..(3)
<223> OTHER INFORMATION: Phosphonoacetate Internucleotide Linkage
<220> FEATURE:
<221> NAME/KEY: misc_feature
<222> LOCATION: (3)..(5)
<223> OTHER INFORMATION: Phosphorothioate Internucleotide Linkages
<220> FEATURE:
<221> NAME/KEY: misc_feature
<222> LOCATION: (5)..(6)
<223> OTHER INFORMATION: Phosphonoacetate Internucleotide Linkage
<220> FEATURE:
<221> NAME/KEY: misc_feature
<222> LOCATION: (6)..(16)
<223> OTHER INFORMATION: Phosphorothioate Internucleotide Linkages
<220> FEATURE:
<221> NAME/KEY: misc_feature
<222> LOCATION: (16)..(17)
<223> OTHER INFORMATION: Phosphonoacetate Internucleotide Linkage
<220> FEATURE:
<221> NAME/KEY: misc_feature
<222> LOCATION: (17)..(21)
<223> OTHER INFORMATION: Phosphorothioate Internucleotide Linkages

<400> SEQUENCE: 29 tcgtcgttt tcggtcgttt t                                              21

<210> SEQ ID NO 30
<211> LENGTH: 22
<212> TYPE: DNA
<213> ORGANISM: Artificial Sequence
<220> FEATURE:
<223> OTHER INFORMATION: C Class synthetic oligonucleotide
<220> FEATURE:
<221> NAME/KEY: misc_feature
<222> LOCATION: (1)..(2)
<223> OTHER INFORMATION: Phosphorothioate Internucleotide Linkages
<220> FEATURE:
```

```
<221> NAME/KEY: misc_feature
<222> LOCATION: (2)..(3)
<223> OTHER INFORMATION: Phosphonoacetate Internucleotide Linkage
<220> FEATURE:
<221> NAME/KEY: misc_feature
<222> LOCATION: (3)..(22)
<223> OTHER INFORMATION: Phosphorothioate Internucleotide Linkages
<220> FEATURE:
<221> NAME/KEY: misc_feature
<222> LOCATION: (22)..(22)
<223> OTHER INFORMATION: 3'-O-methyl-G

<400> SEQUENCE: 30
tcgtcgtttt cggcgcgcgc cg                                              22

<210> SEQ ID NO 31
<211> LENGTH: 22
<212> TYPE: DNA
<213> ORGANISM: Artificial Sequence
<220> FEATURE:
<223> OTHER INFORMATION: C Class synthetic oligonucleotide
<220> FEATURE:
<221> NAME/KEY: misc_feature
<222> LOCATION: (1)..(5)
<223> OTHER INFORMATION: Phosphorothioate Internucleotide Linkages
<220> FEATURE:
<221> NAME/KEY: misc_feature
<222> LOCATION: (5)..(6)
<223> OTHER INFORMATION: Phosphonoacetate Internucleotide Linkage
<220> FEATURE:
<221> NAME/KEY: misc_feature
<222> LOCATION: (6)..(22)
<223> OTHER INFORMATION: Phosphorothioate Internucleotide Linkages
<220> FEATURE:
<221> NAME/KEY: misc_feature
<222> LOCATION: (22)..(22)
<223> OTHER INFORMATION: 3'-O-methyl-G

<400> SEQUENCE: 31
tcgtcgtttt cggcgcgcgc cg                                              22

<210> SEQ ID NO 32
<211> LENGTH: 22
<212> TYPE: DNA
<213> ORGANISM: Artificial Sequence
<220> FEATURE:
<223> OTHER INFORMATION: C Class synthetic oligonucleotide
<220> FEATURE:
<221> NAME/KEY: misc_feature
<222> LOCATION: (1)..(2)
<223> OTHER INFORMATION: Phosphorothioate Internucleotide Linkages
<220> FEATURE:
<221> NAME/KEY: misc_feature
<222> LOCATION: (2)..(3)
<223> OTHER INFORMATION: Phosphonoacetate Internucleotide Linkage
<220> FEATURE:
<221> NAME/KEY: misc_feature
<222> LOCATION: (3)..(5)
<223> OTHER INFORMATION: Phosphorothioate Internucleotide Linkages
<220> FEATURE:
<221> NAME/KEY: misc_feature
<222> LOCATION: (5)..(6)
<223> OTHER INFORMATION: Phosphonoacetate Internucleotide Linkage
<220> FEATURE:
<221> NAME/KEY: misc_feature
<222> LOCATION: (6)..(22)
<223> OTHER INFORMATION: Phosphorothioate Internucleotide Linkages
<220> FEATURE:
<221> NAME/KEY: misc_feature
<222> LOCATION: (22)..(22)
<223> OTHER INFORMATION: 3'-O-methyl-G

<400> SEQUENCE: 32
tcgtcgtttt cggcgcgcgc cg                                              22
```

```
<210> SEQ ID NO 33
<211> LENGTH: 22
<212> TYPE: DNA
<213> ORGANISM: Artificial Sequence
<220> FEATURE:
<223> OTHER INFORMATION: C Class synthetic oligonucleotide
<220> FEATURE:
<221> NAME/KEY: misc_feature
<222> LOCATION: (1)..(22)
<223> OTHER INFORMATION: Phosphorothioate Internucleotide Linkages
<220> FEATURE:
<221> NAME/KEY: misc_feature
<222> LOCATION: (22)..(22)
<223> OTHER INFORMATION: 3'-O-methyl-G

<400> SEQUENCE: 33
tcgtcgtttt cggcgcgcgc cg                                              22
```